(12) United States Patent
Burns et al.

(10) Patent No.: US 11,304,652 B2
(45) Date of Patent: Apr. 19, 2022

(54) MEASUREMENT OF TISSUE VIABILITY

(71) Applicant: BBI Medical Innovations, LLC, Los Angeles, CA (US)

(72) Inventors: Martin F. Burns, Los Angeles, CA (US); Sara Barrington, Thousand Oaks, CA (US); Graham O. Ross, Glen Mills, PA (US)

(73) Assignee: BBI Medical Innovations, LLC, Los Angeles, CA (US)

( * ) Notice: Subject to any disclaimer, the term of this patent is extended or adjusted under 35 U.S.C. 154(b) by 1114 days.

(21) Appl. No.: 15/887,837

(22) Filed: Feb. 2, 2018

(65) Prior Publication Data

US 2018/0220953 A1 Aug. 9, 2018

Related U.S. Application Data

(60) Provisional application No. 62/521,926, filed on Jun. 19, 2017, provisional application No. 62/454,487, filed on Feb. 3, 2017.

(51) Int. Cl.
| | |
|---|---|
| *A61B 5/00* | (2006.01) |
| *A61B 5/0531* | (2021.01) |
| *A61B 5/0537* | (2021.01) |
| *G01R 27/26* | (2006.01) |

(52) U.S. Cl.
CPC ............ *A61B 5/445* (2013.01); *A61B 5/0531* (2013.01); *A61B 5/0537* (2013.01); *A61B 5/4878* (2013.01); *G01R 27/2605* (2013.01)

(58) Field of Classification Search
CPC ... A61B 5/4881; A61B 5/4878; A61B 5/0531; A61B 5/0537; A61B 5/445; A61B 5/7445; A61B 5/6833; G01R 27/2605
See application file for complete search history.

(56) References Cited

U.S. PATENT DOCUMENTS

| | | | |
|---|---|---|---|
| 4,295,009 A | 10/1981 | Weidler | |
| 4,557,271 A * | 12/1985 | Stoller | A61B 5/2415 600/547 |
| 4,857,716 A | 8/1989 | Gombrich et al. | |
| 4,860,753 A | 8/1989 | Amerena | |
| 5,073,126 A | 12/1991 | Kikuchi et al. | |
| 5,284,150 A | 2/1994 | Butterfield et al. | |
| 5,292,341 A | 3/1994 | Snell | |
| 5,367,789 A | 11/1994 | Lamont | |

(Continued)

FOREIGN PATENT DOCUMENTS

| | | |
|---|---|---|
| CA | 2811609 | 11/2011 |
| CA | 2609842 C | 10/2016 |

(Continued)

OTHER PUBLICATIONS

International Search Report dated Jul. 12, 2018, issued in International Patent Application No. PCT/US2018/016736.

(Continued)

*Primary Examiner* — Devin B Henson
(74) *Attorney, Agent, or Firm* — Arnold & Porter Kaye Scholer LLP

(57) ABSTRACT

The present disclosure provides apparatuses and methods for measuring sub-epidermal moisture as an indication of tissue viability and providing information regarding the location of a boundary of non-viable tissue.

12 Claims, 9 Drawing Sheets

(56) References Cited

U.S. PATENT DOCUMENTS

| | | | |
|---|---|---|---|
| 5,815,416 A | 9/1998 | Liebmann et al. | |
| 5,904,581 A | 5/1999 | Pope et al. | |
| 6,223,088 B1 | 4/2001 | Scharnberg et al. | |
| 6,312,263 B1 | 11/2001 | Higuchi et al. | |
| 6,330,479 B1 | 12/2001 | Stauffer | |
| 6,370,426 B1 | 4/2002 | Campbell et al. | |
| 6,434,422 B1 | 8/2002 | Tomoda et al. | |
| 6,577,700 B1 | 6/2003 | Fan et al. | |
| 6,634,045 B1 | 10/2003 | DuDonis et al. | |
| 6,738,798 B1 | 5/2004 | Ploetz et al. | |
| 6,756,793 B2 | 6/2004 | Hirono et al. | |
| 6,963,772 B2 | 11/2005 | Bloom et al. | |
| 7,079,899 B2 | 7/2006 | Petrofsky | |
| 7,315,767 B2 | 1/2008 | Caduff et al. | |
| 7,402,135 B2 | 7/2008 | Leveque et al. | |
| 7,783,344 B2 | 8/2010 | Lackey et al. | |
| 8,011,041 B2 | 9/2011 | Hann | |
| 8,060,315 B2 | 11/2011 | Brosette et al. | |
| 8,355,925 B2 | 1/2013 | Rothman et al. | |
| 8,390,583 B2 | 3/2013 | Forutanpour et al. | |
| 8,494,617 B2 | 7/2013 | Baker, Jr. et al. | |
| 8,925,392 B2 | 1/2015 | Esposito et al. | |
| 9,028,407 B1 | 5/2015 | Bennett-Guerrero | |
| 9,095,305 B2 | 8/2015 | Engler et al. | |
| 9,220,455 B2 * | 12/2015 | Sarrafzadeh | A61B 5/447 |
| 9,271,676 B2 | 3/2016 | Alanen et al. | |
| 9,398,879 B2 | 7/2016 | Sarrafzadeh et al. | |
| 9,675,289 B2 | 6/2017 | Heaton | |
| 9,763,596 B2 | 9/2017 | Tonar et al. | |
| 9,949,683 B2 | 4/2018 | Afentakis | |
| 9,980,673 B2 | 5/2018 | Sarrafzadeh et al. | |
| 10,085,643 B2 | 10/2018 | Bandic et al. | |
| 10,166,387 B2 | 1/2019 | Bergelin et al. | |
| 10,178,961 B2 | 1/2019 | Tonar et al. | |
| 10,182,740 B2 | 1/2019 | Tonar et al. | |
| 10,188,340 B2 | 1/2019 | Sarrafzadeh et al. | |
| 10,194,856 B2 | 2/2019 | Afentakis et al. | |
| 10,206,604 B2 | 2/2019 | Bergelin et al. | |
| 10,226,187 B2 | 3/2019 | Al-Ali et al. | |
| 10,278,636 B2 | 5/2019 | Wu et al. | |
| 10,285,898 B2 | 5/2019 | Douglas et al. | |
| 10,307,060 B2 | 6/2019 | Tran | |
| 10,342,482 B1 | 7/2019 | Lisy et al. | |
| 10,383,527 B2 | 8/2019 | Al-Ali | |
| 10,420,602 B2 | 9/2019 | Horton et al. | |
| 10,441,185 B2 | 10/2019 | Rogers et al. | |
| 10,448,844 B2 | 10/2019 | Al-Ali et al. | |
| 10,463,293 B2 | 11/2019 | Maharbiz et al. | |
| 10,485,447 B2 | 11/2019 | Tonar et al. | |
| 2001/0051783 A1 | 12/2001 | Edwards et al. | |
| 2002/0016535 A1 | 2/2002 | Martin et al. | |
| 2002/0070866 A1 | 6/2002 | Newham | |
| 2002/0112898 A1 | 8/2002 | Honda et al. | |
| 2002/0143262 A1 | 10/2002 | Bardy | |
| 2003/0009244 A1 | 1/2003 | Engleson et al. | |
| 2003/0036674 A1 | 2/2003 | Bouton | |
| 2003/0036713 A1 | 2/2003 | Bouton et al. | |
| 2003/0110662 A1 | 6/2003 | Gilman et al. | |
| 2003/0116447 A1 | 6/2003 | Surridge et al. | |
| 2003/0139255 A1 | 7/2003 | Lina | |
| 2004/0041029 A1 | 3/2004 | Postman et al. | |
| 2004/0046668 A1 | 3/2004 | Smith et al. | |
| 2004/0054298 A1 | 3/2004 | Masuo et al. | |
| 2004/0080325 A1 | 4/2004 | Ogura | |
| 2004/0133092 A1 | 7/2004 | Kain | |
| 2004/0171962 A1 | 9/2004 | Leveque et al. | |
| 2004/0176754 A1 | 9/2004 | Island et al. | |
| 2004/0236200 A1 | 11/2004 | Say et al. | |
| 2004/0254457 A1 | 12/2004 | Van Der Weide | |
| 2005/0027175 A1 | 2/2005 | Yang | |
| 2005/0070778 A1 | 3/2005 | Lackey et al. | |
| 2005/0086072 A1 | 4/2005 | Fox, Jr. et al. | |
| 2005/0096513 A1 | 5/2005 | Ozguz et al. | |
| 2005/0177061 A1 | 8/2005 | Alanen et al. | |
| 2005/0203435 A1 | 9/2005 | Nakada | |
| 2005/0215918 A1 | 9/2005 | Frantz et al. | |
| 2005/0245795 A1 | 11/2005 | Goode et al. | |
| 2005/0251418 A1 | 11/2005 | Fox, Jr. et al. | |
| 2006/0052678 A1 | 3/2006 | Drinan et al. | |
| 2006/0058593 A1 * | 3/2006 | Drinan | A61B 5/6807 600/301 |
| 2006/0097949 A1 | 5/2006 | Luebke et al. | |
| 2006/0206013 A1 | 9/2006 | Rothman et al. | |
| 2007/0106172 A1 | 5/2007 | Abreu | |
| 2007/0179585 A1 | 8/2007 | Chandler et al. | |
| 2007/0191273 A1 * | 8/2007 | Ambati | A61K 38/177 514/44 R |
| 2007/0213700 A1 | 9/2007 | Davison et al. | |
| 2008/0009764 A1 | 1/2008 | Davies | |
| 2008/0015894 A1 | 1/2008 | Miller et al. | |
| 2008/0048680 A1 | 2/2008 | Hargreaves et al. | |
| 2008/0259577 A1 | 10/2008 | Hu et al. | |
| 2008/0278336 A1 | 11/2008 | Ortega et al. | |
| 2009/0104797 A1 | 4/2009 | Tseng et al. | |
| 2009/0124924 A1 | 5/2009 | Eror et al. | |
| 2009/0189092 A1 | 7/2009 | Aoi et al. | |
| 2009/0285785 A1 | 11/2009 | Jimi et al. | |
| 2010/0017182 A1 | 1/2010 | Voros et al. | |
| 2010/0030167 A1 | 2/2010 | Thirstrup et al. | |
| 2010/0042389 A1 | 2/2010 | Farruggia et al. | |
| 2010/0113979 A1 | 5/2010 | Sarrafzadeh et al. | |
| 2010/0298687 A1 | 11/2010 | Yoo et al. | |
| 2010/0312233 A1 | 12/2010 | Furnish et al. | |
| 2010/0324455 A1 | 12/2010 | Rangel et al. | |
| 2010/0324611 A1 | 12/2010 | Deming et al. | |
| 2011/0046505 A1 | 2/2011 | Cornish et al. | |
| 2011/0184264 A1 | 7/2011 | Galasso, Jr. et al. | |
| 2011/0191122 A1 | 8/2011 | Kharraz Tavakol et al. | |
| 2011/0237926 A1 * | 9/2011 | Jensen | A61B 5/0537 600/393 |
| 2011/0263950 A1 | 10/2011 | Larson et al. | |
| 2011/0301441 A1 | 12/2011 | Bandic et al. | |
| 2011/0313311 A1 | 12/2011 | Gaw | |
| 2012/0029410 A1 | 2/2012 | Koenig et al. | |
| 2012/0061257 A1 | 3/2012 | Yu et al. | |
| 2012/0078088 A1 | 3/2012 | Whitestone et al. | |
| 2012/0150011 A1 | 6/2012 | Besio | |
| 2012/0179006 A1 | 7/2012 | Jansen et al. | |
| 2012/0190989 A1 * | 7/2012 | Kaiser | A61B 5/0031 600/476 |
| 2012/0271121 A1 | 10/2012 | Della Torre et al. | |
| 2013/0041235 A1 * | 2/2013 | Rogers | A61B 5/1107 600/306 |
| 2013/0072870 A1 | 3/2013 | Heppe et al. | |
| 2013/0121544 A1 * | 5/2013 | Sarrafzadeh | A61B 5/445 382/128 |
| 2013/0123587 A1 | 5/2013 | Sarrafzadeh et al. | |
| 2013/0137951 A1 | 5/2013 | Chuang et al. | |
| 2013/0253285 A1 | 9/2013 | Bly et al. | |
| 2013/0261496 A1 | 10/2013 | Engler et al. | |
| 2013/0301255 A1 | 11/2013 | Kim et al. | |
| 2013/0310440 A1 | 11/2013 | Duskin et al. | |
| 2013/0333094 A1 | 12/2013 | Rogers et al. | |
| 2013/0338661 A1 | 12/2013 | Behnke, II | |
| 2014/0121479 A1 | 5/2014 | O'Connor et al. | |
| 2014/0142984 A1 | 5/2014 | Wright et al. | |
| 2014/0200486 A1 | 7/2014 | Bechtel et al. | |
| 2014/0273025 A1 | 9/2014 | Hurskainen et al. | |
| 2014/0275823 A1 * | 9/2014 | Lane | A61B 5/259 600/301 |
| 2014/0288397 A1 * | 9/2014 | Sarrafzadeh | A61B 5/447 600/306 |
| 2014/0298928 A1 | 10/2014 | Duesterhoft et al. | |
| 2014/0316297 A1 | 10/2014 | McCaughan et al. | |
| 2014/0318699 A1 | 10/2014 | Longinotti-Buitoni et al. | |
| 2015/0002168 A1 | 1/2015 | Kao et al. | |
| 2015/0009168 A1 | 1/2015 | Levesque et al. | |
| 2015/0094548 A1 | 4/2015 | Sabatini et al. | |
| 2015/0186607 A1 | 7/2015 | Gileijnse et al. | |
| 2015/0230863 A1 | 8/2015 | Youngquist et al. | |
| 2015/0363567 A1 | 12/2015 | Pettus | |
| 2015/0366499 A1 | 12/2015 | Sarrafzadeh et al. | |
| 2015/0371522 A1 | 12/2015 | Mravyan et al. | |

(56) References Cited

U.S. PATENT DOCUMENTS

| | | |
|---|---|---|
| 2016/0038055 A1 | 2/2016 | Wheeler et al. |
| 2016/0072308 A1 | 3/2016 | Nyberg et al. |
| 2016/0100790 A1 | 4/2016 | Cantu et al. |
| 2016/0101282 A1 | 4/2016 | Bergelin et al. |
| 2016/0174871 A1 | 6/2016 | Sarrafzadeh et al. |
| 2016/0220172 A1 | 8/2016 | Sarrafzadeh et al. |
| 2016/0270968 A1* | 9/2016 | Stanford ............ A61F 13/0236 |
| 2016/0278692 A1 | 9/2016 | Larson et al. |
| 2016/0296268 A1 | 10/2016 | Gee et al. |
| 2016/0310034 A1* | 10/2016 | Tonar .................. A61B 5/4875 |
| 2016/0338591 A1* | 11/2016 | Lachenbruch ....... A61B 5/7405 |
| 2017/0007153 A1 | 1/2017 | Tonar et al. |
| 2017/0014044 A1* | 1/2017 | Tonar .................... A61B 5/447 |
| 2017/0014045 A1 | 1/2017 | Tonar et al. |
| 2017/0156658 A1 | 6/2017 | Maharbiz et al. |
| 2017/0172489 A1* | 6/2017 | Afentakis .............. A61B 5/447 |
| 2017/0188841 A1 | 7/2017 | Ma et al. |
| 2017/0238849 A1 | 8/2017 | Chapman et al. |
| 2017/0255812 A1 | 9/2017 | Kwon |
| 2017/0311807 A1 | 11/2017 | Fu et al. |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0060602 A1 | 2/2019 | Tran et al. |
| 2019/0104981 A1 | 4/2019 | Sarrafzadeh et al. |
| 2019/0104982 A1 | 4/2019 | Dunn et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |

FOREIGN PATENT DOCUMENTS

| | | |
|---|---|---|
| CN | 204119175 U | 1/2015 |
| CN | 104567657 A | 4/2015 |
| CN | 208111467 U | 11/2018 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2584808 A | 12/2020 |
| JP | 2003-169788 A | 6/2003 |
| JP | 2003-290166 A | 10/2003 |
| JP | 2005-52227 | 3/2005 |
| JP | 4418419 | 2/2010 |
| JP | 2013-528428 | 7/2013 |
| JP | 2013-198639 A | 10/2013 |
| JP | 2015-509028 | 3/2015 |
| JP | 2016-519969 | 7/2016 |
| JP | 2016-527943 A | 9/2016 |
| KR | 10-2014-0058445 | 5/2014 |
| WO | 96/10951 A1 | 4/1996 |
| WO | 2002/080770 A1 | 10/2002 |
| WO | 2004/105602 A1 | 12/2004 |
| WO | 2006/029035 A1 | 3/2006 |
| WO | 2007/098762 A1 | 9/2007 |
| WO | 2009/144615 A1 | 12/2009 |
| WO | 2010/060102 A2 | 5/2010 |
| WO | 2011/022418 A2 | 2/2011 |
| WO | 2011/080080 A1 | 7/2011 |
| WO | 2011/080262 A1 | 7/2011 |
| WO | 2011/143071 A2 | 11/2011 |
| WO | 2013/116242 A2 | 8/2013 |
| WO | 2014/186894 A1 | 11/2014 |
| WO | 2015/003015 A2 | 1/2015 |
| WO | 2015/168720 A1 | 11/2015 |
| WO | 2015/169911 A1 | 11/2015 |
| WO | 2015/195720 A1 | 12/2015 |
| WO | WO 2015/195720 A1 * | 12/2015 ............... A61B 5/05 |
| WO | 2016/172263 A1 | 10/2016 |
| WO | 2016/172264 A1 | 10/2016 |
| WO | 2017/032393 A1 | 3/2017 |
| WO | 2017/214188 A1 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Bergstrom et al., "Pressure Ulcers in Adults: Prediction and Prevention," *Clinical Practice Guideline—Quick Reference Guide for Clinicians*, 117 (1992).

Alanen, "Measurement of Hydration in the Stratum Corneum with the MoistureMeter and Comparison with the Corneometer," *Skin Research and Technology*, 10:32-37 (2004).

Alberts et al., "The Extracellular Matrix of Animals," *Molecular Biology of the Cell*, 4th ed., pp. 1065-1127 (2002).

Allman et al., "Pressure Ulcer Risk Factors Among Hospitalized Patiens with Activity Limitation," *JAMA*, 273:865-870 (1995).

Anonymous, "Recommended Practices for Positioning the Patient in the Perioperative Practice Setting," in *Perioperative Standards, Recommended Practices, and Guidelines*, AORN, Inc., 525-548 (2006).

Arao et al., "Morphological Characteristics of the Dermal Papillae In the Development of Pressure Sores," *World Wide Wounds*, (1999).

(56) References Cited

OTHER PUBLICATIONS

Australian Intellectual Property Office, Office Action dated May 1, 2014 for corresponding Australian patent application No. 2011253253 (pp. 1-10) and pending claims (pp. 11-15) pp. 1-15.
Australian Patent Office, Office Action dated Jun. 1, 2015, for corresponding Australian Patent Application No. 2011253253 (pp. 1-4) and claims (pp. 5-10) pp. 1-10.
Bader et al., "Effect of Externally Applied Skin Surface Forces on Tissue Vasculature," *Archives of Physical Medicine and Rehabilitation*, 67(11):807-11 (1986).
Barnes, "Moisture Meters for Use on Thin Lumber and Veneers," *Moisture Register Co.*, 1-5 (1956)
Bates-Jensen et al., "Subepidermal Moisture Predicts Erythema and Stage 1 Pressure Ulcers in Nursing Home Residents: A Pilot Study," *Journal of the American Geriatric Society*, 55:1199-1205 (2007).
Bates-Jensen et al., "Subepidermal moisture differentiates erythema and stage 1 pressure ulcers in nursing home residents," *Wound Repair Regeneration*, 16:189-197 (2008).
Bates-Jensen et al., "Subepidermal Moisture Is Associated With Early Pressure Ulcer Damage in Nursing Home Residents With Dark Skin Tones; Pilot Findings," *Journal of Wound Ostomy and Continence Nursing*, 36(3):277-284 (2009).
Bergstrand et al., "Pressure-induced Vasodilation and Reactive Hyperemia at Different Depths in Sacral Tissue Under Clinically Relevant Conditions," *Microcirculation*, 21:761-771 (2014).
Brem et al. "High cost of stage IV pressure ulcers," *American Journal of Surgery*, 200:473-477 (2010).
Brienza et al., "Friction-Induced Skin Injuries—Are They Pressure Ulcers?," *Journal of Wound Ostomy and Continence Nursing*, 42(1):62-64 (2015).
Carmo-Araujo et al., "Ischaemia and reperfusion effects on skeletal muscle tissue: morphological and histochemical studies," *International Journal of Experimental Pathology*, 88:147-154 (2007).
Ceelen et al., "Compression-induced damage and internal tissue strains are related," *Journal of Biomechanics*, 41:3399-3404 (2008).
Ching et al., "Tissue electrical properties monitoring for the prevention of pressure sore," *Prosthetics and Orthotics International*, 35(4):386-394 (2011).
Clendenin et al., "Inter-operator and inter-device agreement and reliability of the SEM Scanner," *Journal of Tissue Viability*, 24(1):17-23 (2015).
De Lorenzo et al., "Predicting body cell mass with bioimpedance by using theoretical methods: a technological review," *Journal of Applied Physiology*, 82(5):1542-1558 (1997).
Demarre et al., "The cost of pressure ulcer prevention and treatment in hospitals and nursing homes in Flanders: A cost-of-illness study," *International Journal of Nursing Studies*, 1-14 (2015).
Dodde et al., "Bioimpedance of soft tissue under compression," *Physiology Measurement*, 33(6): 1095-1109 (2012)
DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).
Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).
DuPont, "Pyralux® FR Copper-clad Laminate," webpage, Retrieved from: www2.dupont.com/Pyraluxlen_US/productsllaminate/FR/pyralux_fr.html, pp. 1-2 (2012).
Eberlein-Gonska et al., "The Incidence and Determinants of Decubitus Ulcers in Hospital Care: An Analysis of Routine Quality Management Data at a University Hospital," *Deutsches Arzteblatt International*, 110(33-34):550-556 (2013).
European Patent Office, ESSR issued on Aug. 22, 2014 for corresponding European Patent Application No. 117811061.4 (pp. 1-7) and pending claims (pp. 3-10) pp. 1-10.
European Patent Office, Office Action dated Jul. 13, 2015, for corresponding European Patent Application No. 117811061.4 (pp. 1-5) and claims (pp. 6-9) pp. 1-9.
Extended European Search Report dated Aug. 19, 2016, in European Patent Application No. 16169670.

Extended European Search Report dated Sep. 19, 2016, in European Patent Application No. 16166483.4.
Extended European Search Report dated Mar. 13, 2017, in European Patent Application No. 16196899.5.
Gabriel, "Compilation of the Dielectric Properties of Body Tissues at Rf and Microwave Frequencies Report," *Occupational and Environmental Health Directorate*, (1996).
Gabriel et al., "The dielectric properties of biological tissues: II. Measurements in the frequency range 10 Hz to 20 GHz," *Physics in Medicine and Biology*, 41:2251-69 (1996).
Gardiner et al., "Incidence of hospital-acquired pressure ulcers—a population-based cohort study," *International Wound Journal*, 11(6):696-700 (2014)
Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).
Gonzalez-Correa et al., "Electrical bioimpedance readings increase with higher pressure applied to the measuring probe," *Physiology Measurement*, 26:S39-S47 (2005).
Guihan et al., "Assessing the feasibility of subepidermal moisture to predict erythema and stage 1 pressure ulcers in persons with spinal cord injury: A pilot study," *Journal of Spinal Cord Medicine*, 35(1):46-52 (2012).
Harrow, "Subepidermal moisture surrounding pressure ulcers in persons with a spinal cord injury: A pilot study," *Journal of Spinal Cord Medicine*, 37(6):719-728 (2014).
Houwing et al., "Pressure-induced skin lesions in pigs: reperfusion injury and the effects of vitamin E," *Journal of Wound Care*, 9(1):36-40 (2000).
Huang et al., "A device for skin moisture and environment humidity detection," *Sensors and Actuators B: Chemical*, 206-212 (2008).
International Search Report dated Apr. 12, 2018, issued in International Patent Application No. PCT/US2018/016731.
International Search Report dated Apr. 12, 2018, issued in International Patent Application No. PCT/US2018/016738.
International Search Report dated Apr. 26, 2018, issued in International Patent Application No. PCT/US2018/016741.
International Search Report and Written Opinion dated Feb. 9, 2012 for International Patent Application No. PCT/US2011/035618.
International Search Report and Written Opinion dated Jul. 22, 2016, for International Patent Application No. PCT/US2016/28515.
International Search Report and Written Opinion dated Jul. 26, 2016, for International Patent Application No. PCT/US2016/28516.
Jan et al., "Local cooling reduces skin ischemia under surface pressure in rats: an assessment by wavelet analysis of laser Doppler blood flow oscillations," *Physiology Measurement*, 33(10):1733-1745 (2012).
Jaskowski, "Evaluation of the Healing Process of Skin Wounds by Means of Skin Absolute Value of Electrical Impedance," *Dermatol. Mon.schr.*, 172(4):223-228 (1986).
Jiang et al., "Expression of cytokines, growth factors and apoptosis-related signal molecules in chronic pressure ulcer wounds healing," *Spinal Cord*, 52(2):145-151 (2014).
Jiang et al., "Ischemia-Reperfusion Injury-Induced Histological Changes Affecting Early Stage Pressure Ulcer Development in a Rat model," *Ostomy Wound Management*, 57:55-60 (2011).
Jiricka et al., "Pressure Ulcer Risk factors in an ICU Population," *American Journal of Critical Care*, 4:361-367 (1995).
Kanai et al., "Electrical measurement of fluid distribution in legs and arms," *Medical Progress through Technology Journal*, 12:159-170 (1987).
Kasyua et al., "Potential application of in vivo imaging of impaired lymphatic duct to evaluate the severity of pressure ulcer in mouse model," *Scientific Reports*, 4:4173 (2014).
Lee, "CapSense Best Practices," *Application Note* 2394, 1-10 (2007).
Loerakker et al., "The effects of deformation, ischemia, and reperfusion on the development of muscle damage during prolonged loading," *Journal of Applied Physiology*, 111(4):1168-1177 (2011).
Loerakker et al., "Temporal Effects of Mechanical Loading on Deformation-Induced Damage in Skeletal Muscle Tissue," *Annual Review of Biomedical Engineering*, 38(8):2577-2587 (2010).

(56) References Cited

OTHER PUBLICATIONS

Lyder et al., "Quality of Care for Hospitalized Medicare Patients at Risk for Pressure Ulcers," Archives of Internal Medicine, 161:1549-1554 (2001).

Martinsen, "Bioimpedance and Bioelectricity Basics," Elsevier Academic Press, Chapters 1 and 10 (2015).

Mathiesen et al., "Are labour-intensive efforts to prevent pressure ulcers cost-effective?" Journal of Medical Economics, 16(10):1238-1245 (2013).

Matthie et al., "Analytic assessment of the various bioimpedance methods used to estimate body water," Journal of Applied Physiology, 84(5):1801-1816 (1998)

Miller et al., "Lymphatic Clearance during Compressive Loading," Lymphology, 14(4):161-166 (1981).

Moore et al., "A randomised controlled clinical trial of repositioning, using the 30° tilt, for the prevention of pressure ulcers," Journal of Clinical Nursing, 20:2633-2644 (2011).

Moore et al., "Pressure ulcer prevalence and prevention practices in care of the older person in the Republic of Ireland," Journal of Clinical Nursing, 21:362-371 (2012).

Moore et al., "A review of PU prevalence and incidence across Scandinavia, Iceland and Ireland (Part I)", Journal of Wound Care, 22(7):361-362, 364-368 (2013).

Mulasi, "Bioimpedance at the Bedside: Current Applications, Limitations, and Opportunities," Nutritional Clinical Practice, 30(2):180-193 (2015).

National Pressure Ulcer Advisory Panel et al., "Prevention and Treatment of Pressure Ulcers: Clinical Practice Guideline," Cambridge Media, (2014).

Nixon et al., "Pathology, diagnosis, and classification of pressure ulcers: comparing clinical and imaging techniques," Wound Repair and Regeneration, 13(4):365-372 (2005).

Nuutinen et al., "Validation of a new dielectric device to asses changes of tissue water in skin and subcutaneous fat," Physiological Measurement, 25:447-454 (2004).

O'Goshi, "Skin conductance; validation of Skicon-200EX compared to the original model, Skicon-100," Skin Research and Technology, 13:13-18 (2007).

Oomens et al., "Pressure Induced Deep Tissue Injury Explained," Annual Review of Biomedical Engineering, 43(2):297-305 (2015).

Scallan et al., "Chapter 4: Pathophysiology of Edema Formation," Capillary Fluid Exchange: Regulation, Functions, and Pathology, 47-61 (2010).

Schultz et al., "Extracellular matrix: review of its role in acute and chronic wounds," World Wide Wounds, 1-20 (2005).

Schwan, "Electrical properties of tissues and cells," Advances in Biology and Medical Physics, 15:148-199 (1957)

Sener et al., "Pressure ulcer-induced oxidative organ injury is ameliorated by beta-glucan treatment in rats," International Immunopharmacology, 6(5):724-732 (2006).

Sewchuck et al., "Prevention and Early Detection of Pressure Ulcers in Patients Undergoing Cardiac Surgery," AORN Journal, 84(1):75-96 (2006).

Sprigle et al., "Analysis of Localized Erythema Using Clinical Indicators and Spectroscopy," Ostomy Wound Management, 49:42-52 (2003).

Stekelenburg et al., "Deep Tissue Injury: How Deep is Our Understanding?" Archives of Physical Medicine Rehabilitation, 89(7):1410-1413 (2008).

Stekelenburg et al., "Role of ischemia and deformation in the onset of compression-induced deep tissue injury: MRI-based studies in a rat model," Journal of Applied Physiology, 102:2002-2011 (2007).

Swisher et al., "Impedance sensing device enables early detection of pressure ulcers in vivo," Nature Communications, 6:6575-6584 (2015).

Thomas et al., "Hospital-Acquired Pressure Ulcers and Risk of Death," Journal of the American Geriatrics Society, 44:1435-1440 (1996).

Valentinuzzi et al., "Bioelectrical Impedance Techmques in Medicine. Part II: Monitoring of Physiological Events by Impedance," Critical Reviews in Biomedical Engineering, 24(4-6):353-466 (1996).

Vangilder et al., "Results of Nine International Pressure Ulcer Prevalence Surveys: 1989 to 2005," Ostomy Wound Management, 54(2):40-54 (2008).

Wagner et al., "Bioelectrical Impedance as a Discriminator of Pressure Ulcer Risk," Advances in Wound Care, 9(2):30-37 (1996).

Wang, "Biomedical System for Monitoring Pressure Ulcer Development," UCLA Electronic Theses and Dissertations, California, USA, pp. 1-123 (2013).

Watanabe et al, "CT analysis of the use of the electrical impedance technique to estimate local oedema in the extremities in patients with lymphatic obstruction," Medical and Biological Engineering and Computing, 36(1):60-65 (1998).

Weiss, "Tissue destruction by neutrophils," The New England Journal of Medicine, 320(6):365-76 (1989)

Black et al., "Differential Diagnosis of Suspected Deep Tissue Injury," International Wound Journal, 13(4):531-539 (2015).

Brem et al., "Protocol for the Successful Treatment of Pressure Ulcers," The American Journal of Surgery, 188 (Suppl. To Jul. 2004):9S-17S (2004).

Extended European Search Report dated Oct. 25, 2019, in European Patent Application No. 19186393.5.

Extended European Search Report dated Nov. 19, 2019, in European Patent Application No. 19190000.0.

Extended European Search Report dated Feb. 6, 2020, in European Patent Application No. 18748733.5.

Extended European Search Report dated Feb. 10, 2020, in European Patent Application No. 18748025.6.

Extended European Search Report dated Feb. 10, 2020, in European Patent Application No. 18748512.3.

Extended European Search Report dated Jun. 24, 2020, in European Patent Application No. 18747707.0.

Ford, "Hospice Wins Award for Innovation in Pressure Ulcer Prevention," Nursing Times, downloaded and printed on Apr. 18, 2020, from https://www.nursingtimes.net/news/research-and-innovation/hospice-wins-award-for-innovation-in-pressure-ulcer-prevention-30-11-2018/ (2018).

Great Britain Search Report dated Apr. 27, 2020, in Great Britain Patent Application No. GB2002889.0.

International Search Report dated Mar. 9, 2020, issued in International Patent Application No. PCT/US2019/055655.

International Search Report dated Dec. 8, 2020, issued in International Patent Application PCT/US2020/051134.

Liu et al., "A Systematic Review of Electrical Stimulation for Pressure Ulcer Prevention and Treatment in People with Spinal Cord Injuries," The Journal of Spinal Cord Medicine, 37(6):703-718 (2014)

Moore et al., "Subepidermal Moisture (SEM) and Bioimpedance: A Literature Review of a Novel Method for Early Detection of Pressure-Induced Tissue Damage (Pressure Ulcers)," International Wound Journal, 14(2):331-337 (2016).

Moore et al., "SEM Scanner Made Easy," Wounds International, pp. 1-6, available at www.woundsinternational.com (2018).

Oliveira, "The Accuracy of Ultrasound, Thermography, Photography and Sub-Epidermal Moisture as a Predictor of Pressure Ulcer Presence—a Systematic Review," RCSI, School of Nursing thesis (2015).

Rotaru et al., "Friction between Human Skin and Medical Textiles for Decubitus Prevention," Tribology International, 65:91-96 (2013).

Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49 pp. (Aug. 2019).

Supplementary Partial European Search Report dated Jan. 27, 2020, in European Patent Application No. 18747707.

Thomas, "Prevention and Treatment of Pressure Ulcers," J. Am. Med. Dir. Assoc., 7:46-59 (2006).

Truong et al., "Pressure Ulcer Prevention in the Hospital Setting Using Silicone Foam Dressings," Cureus, 8(8):e730, pp. 1-6 (2016).

(56) References Cited

OTHER PUBLICATIONS

Tur et al., "Topical Hydrogen Peroxide Treatment of Ischemic Ulcers in the Guinea Pig: Blood Recruitment in Multiple Skin Sites," *J. Am. Acad. Dermatol.*, 33:217-221 (1995).
Vowden et al., "Diabetic Foot Ulcer or Pressure Ulcer? That Is the Question," *The Diabetic Foot Journal*, 18:62-66 (2015).
Wang et al., "A Wireless Biomedical Instrument for Evidence-Based Tissue Wound Characterization," *Wireless Health*, pp. 222-223 (2010).
Zanibbi, "Pattern Recognition: An Overview," downloaded from https://www.cs.rit.edu/~rlaz/prec20092/slides/Overview.pdf, 30 pp. (2010).
International Search Report dated May 29, 2019, issued in International Patent Application No. PCT/US2019/017226.
International Search Report dated Sep. 10, 2018, issued in International Patent Application No. PCT/US2018/038055.
International Search Report dated Jan. 29, 2019, issued in International Patent Application No. PCT/US2018/061494.
International Search Report dated Feb. 5, 2019, issued in International Patent Application No. PCT/US2018/064527.
International Search Report dated Feb. 11, 2019, issued in International Patent Application No. PCT/US2018/061497.
Bates-Jensen et al., "Subepidermal Moisture Detection of Pressure Induced Tissue Damage on the Trunk: The Pressure Ulcer Detection Study Outcomes," *Wound Repair and Regeneration*, 25:502-511 (2017).
Great Britain Search Report dated Jun. 28, 2021, in Great Britain Patent Application No. GB2106848.1.
International Search Report dated Aug. 17, 2021, issued in International Patent Application PCT/US2021/023818.
Supplementary European Search Report dated Jul. 13, 2021, in European Patent Application No. 18887039.

\* cited by examiner

MEASUREMENT OF TISSUE VIABILITY

CROSS-REFERENCE TO RELATED APPLICATIONS

This application claims the benefit of priority of U.S. Provisional Application 62/454,487 filed Feb. 3, 2017, and U.S. Provisional Application 62/521,926 filed Jun. 19, 2017, each of which is herein incorporated by reference in its entirety.

FIELD

The present disclosure provides apparatus and methods for measuring type and degree of tissue damage around a burn or other type of wound.

BACKGROUND

Serious wounds and burns may have regions of various degrees of damage surrounding the wound site. Effective treatment may require removal of non-viable tissue, yet it can be difficult to visually assess tissue viability. For an open wound such as a burn, there may be a region of non-viable tissue around the immediate wound while further away the tissue may be less damaged and characterized by swelling known as "edema" yet viable and likely to recover.

A common method of burn evaluation assesses the visual and tactile characteristics, namely wound appearance, capillary blanching and refill, capillary staining, and burn wound sensibility to light touch and pinprick. Estimation of the burn depth is difficult. In addition, burn wounds are dynamic and can progress over time and the changes do not immediately become visually apparent.

SUMMARY

In an aspect, the present disclosure provides for, and includes, an apparatus for mapping areas of damage around a wound, the apparatus comprising: a plurality of electrodes embedded on a substrate configured to be placed over an area of tissue that includes the wound, where combinations of the electrodes are capable of forming a plurality of virtual capacitive sensors and each of the virtual capacitive sensors is configured to measure a capacitance of a region of tissue proximate to the respective virtual capacitive sensor, a plurality of visual indicators embedded on the substrate, a drive circuit electronically coupled to the electrodes and visual indicators, a processor electronically coupled to the drive circuit, and a non-transitory computer-readable medium electronically coupled to the processor and comprising instructions stored thereon that, when executed on the processor, perform the steps of: receiving information regarding the measured capacitance from a subset of the plurality of virtual capacitive sensors via the drive circuit, determining a boundary between viable and non-viable tissue, and activating via the drive circuit a portion of the plurality of visual indicators to indicate the boundary.

In an aspect, the present disclosure provides for, and includes, an apparatus for determining a depth of a burn wound, the apparatus comprising: a pair of electrodes capable of forming a capacitive sensor that is configured to measure a capacitance of a region of tissue proximate to the pair of electrodes, a drive circuit electronically coupled to the capacitive sensor, a processor electronically coupled to the drive circuit, and a non-transitory computer-readable medium electronically coupled to the processor and comprising instructions stored thereon that, when executed on the processor, perform the steps of: receiving information regarding the measured capacitance from the capacitive sensor via the drive circuit, comparing the information to a data array comprising pairs of capacitances and depths of burns, and determining the depth of the burn wound associated with the measured capacitance.

In an aspect, the present disclosure provides for, and includes, an apparatus for mapping areas of damage around a wound, the apparatus comprising: a plurality of electrodes embedded on a substrate configured to be placed over a portion of an area of tissue that includes the wound, where pairs of the electrodes are capable of forming a capacitive sensor that is configured to measure a capacitance of a region of tissue proximate to the capacitive sensor, a projector capable of projecting a visual indicator onto the area of tissue that includes the wound, a drive circuit electronically coupled to the plurality of electrodes and the projector, a processor electronically coupled to the drive circuit, and a non-transitory computer-readable medium electronically coupled to the processor and comprising instructions stored thereon that, when executed on the processor, perform the steps of: receiving information regarding the measured capacitance from one or more of the formed capacitive sensors, determining a first boundary between a first type of tissue and a second type of tissue, and causing the projector to project the visual indicator to indicate the boundary.

In one aspect, the present disclosure provides for, and includes a method for mapping areas of damage around a wound, the method comprising: obtaining capacitance measurements over an area of a tissue including the wound using a plurality of electrodes; converting each measured capacitance to an associated sub-epidermal moisture (SEM) value; and marking a first boundary encompassing regions of tissue associated with SEM values that are lesser than a first threshold.

BRIEF DESCRIPTION OF THE DRAWINGS

Some aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figure 1A:
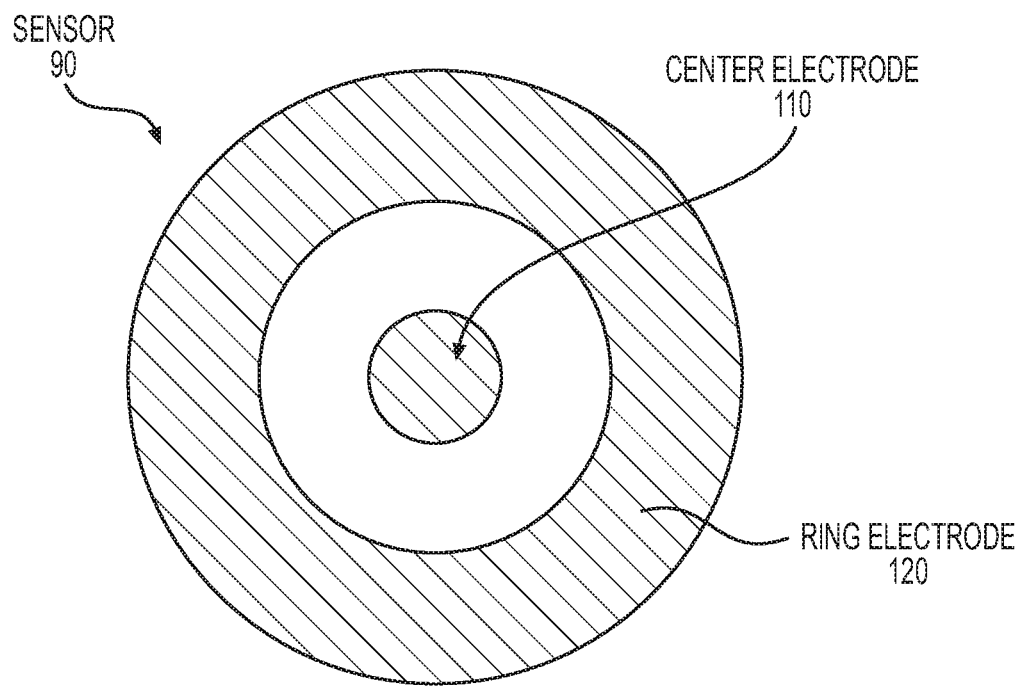
FIG. 1A discloses a toroidal bioimpedance sensor.

The present disclosure describes measurement of various electrical characteristics and derivation of SEM values indicative of the accumulation or depletion of extracellular fluid (ECF), also referred to as intercellular fluid, and the application of this information to the assessment of tissue viability. Examples are provided of application to thermal burns yet are applicable to other types of wounds. These examples are not limiting and the demonstrated principles may be applied to a larger scope of injuries and conditions than the specific example. For example, apparatus and methods disclosed in relation to a $3^{rd}$-degree burn may be used with equal efficacy to an open cut, gangrene, an ulcer, or other similar injury.

Assessment of tissue viability around wounds and burns may be improved by determination of the amount of SEM in the tissue surrounding the actual damage. Typically, the tissue immediately around a wound will exhibit a reduced level of SEM, indicating a lower level of tissue viability. Further out from the wound, the tissue will exhibit an increased level of moisture, or edema. This value may be very high around the edge of the low-moisture tissue, indicating a high degree of damage with a high risk of eventual tissue death. The SEM value may taper off with increasing distance from the wound, where a moderately raised SEM level indicates damage with a higher chance of tissue viability. Mapping the areas of low-viability tissue, as indicated by reduced levels of tissue moisture, and the surrounding area of edema can provide important guidance to a clinician during the treatment of the wound.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments or aspects only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. Nos. 14/827,375 and 15/134,110 are incorporated herein by reference in their entirety.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed disclosure. Thus, the term "consisting essentially of" when used in a claim of this disclosure is not intended to be interpreted to be equivalent to "comprising."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "system" may be a collection of devices in wired or wireless communication with each other.

As used herein, "interrogate" refers to the use of radiofrequency energy to penetrate into a patient's skin.

As used herein, a "patient" may be a human or animal subject.

As used herein, a "$3^{rd}$-degree burn" refers to a full thickness burn that goes through the dermis and affect deeper tissues.

FIG. 1A discloses a toroidal bioimpedance sensor 90. In this exemplary configuration, a center electrode 110 is surrounded by a ring electrode 120. Without being limited to a particular theory, a gap between two electrodes of sensor 90 can affect the depth of field penetration into a substrate below sensor 90. In an aspect, a ground plane (not visible in FIG. 1A), is parallel to and separate from the plane of the electrodes. In one aspect, a ground plan extends beyond the outer diameter of ring electrode 120. Without being limited to a particular theory, a ground plane can limit the field between electrodes 110 and 120 to a single side of the plane of electrodes 110 and 120 that is on the opposite side of the plane of electrodes 110 and 120 from the ground plane.

Figure 1B:
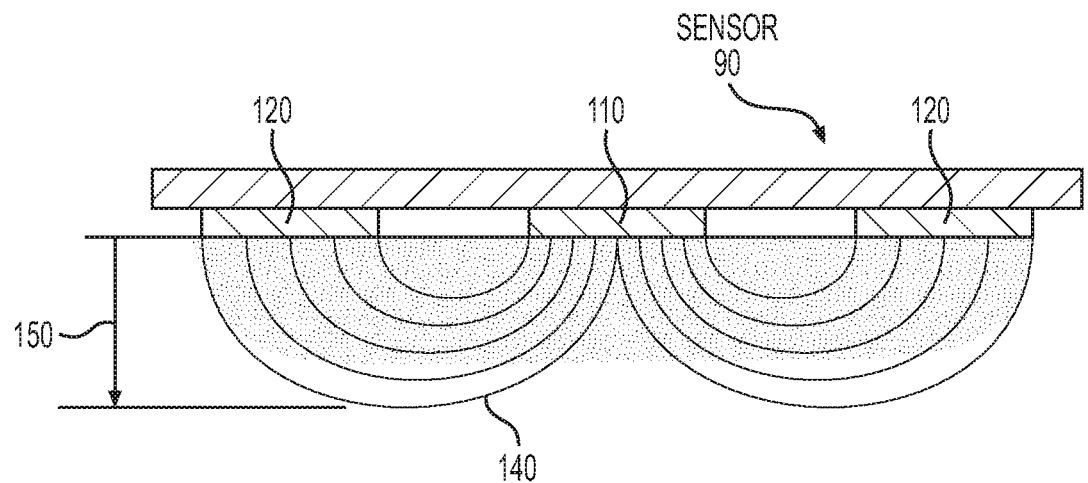
FIG. 1B discloses an idealized field map created by the toroidal sensor of FIG. 1A when activated.

FIG. 1B discloses an idealized field map created by a toroidal sensor of FIG. 1A when activated by a drive circuit (not shown in FIG. 1B). In one aspect, when an electric voltage is applied across two electrodes 110, 120, an electric field 140 is generated between electrodes 110 and 120 that extends outward from the plane of electrodes 110 and 120 to a depth of field 150. In an aspect, the diameter of a center electrode 110, the inner and outer diameters of a ring electrode 120, and the gap between two electrodes 110 and 120 may be varied to change characteristics of field 140, for example the depth of field 150.

In use, a drive circuit can measure an electrical property or parameter that comprises one or more of a resistance, a capacitance, an inductance, an impedance, a reluctance, or other electrical characteristic as sensed by electric field 140. Depending on the type of drive circuit being employed in an apparatus, a sensor of an apparatus may be a bipolar radiofrequency sensor, a bioimpedance sensor, a capacitive sensor, or an SEM sensor. In an aspect, the measured electrical parameter is related to the moisture content of the epidermis of a patient at a depth that is determined by the geometry of electrodes 110 and 120, the frequency and strength of electrical field 140, and other operating characteristics of an apparatus drive circuit. In one aspect, the measured moisture content is equivalent to the SEM content with a value on a predetermined scale. In an aspect, a predetermined scale may range from 0 to 20, such as from 0 to 1, from 0 to 2, from 0 to 3, from 0 to 4, from 0 to 5, from 0 to 6, from 0 to 7, from 0 to 8, from 0 to 9, from 0 to 10, from 0 to 11, from 0 to 12, from 0 to 13, from 0 to 14, from 0 to 15, from 0 to 16, from 0 to 17, from 0 to 18, from 0 to 19. In one aspect, a predetermined scaled can be scaled by a factor or a multiple based on the values provided herein.

Figure 1C:
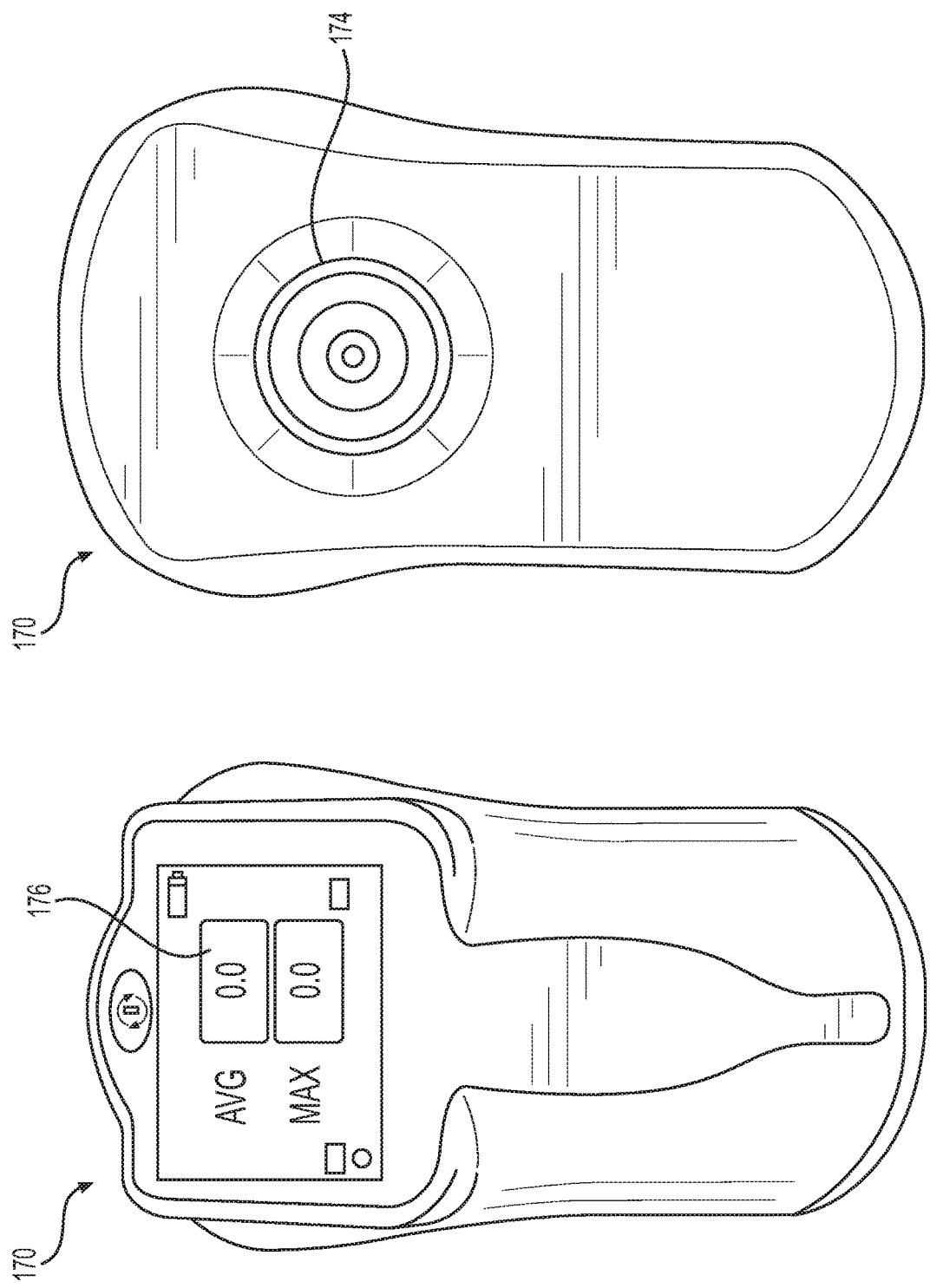
FIG. 1C discloses a SEM scanner that comprises the sensor of FIG. 1A.

FIG. 1C provides top and bottom views of a SEM scanner 170 that comprises electronics that drive sensor 174, which is similar to sensor 90 of FIG. 1A, and measure a capacitance between electrodes 110 and 120. This capacitance is converted to a SEM value that is displayed on display 176.

These aspects of sensor 90 and SEM scanner 170 are disclosed in WO 2016/172263, from which the U.S. patent application Ser. No. 15/134,110 was filed as a national phase entry.

Figure 2:
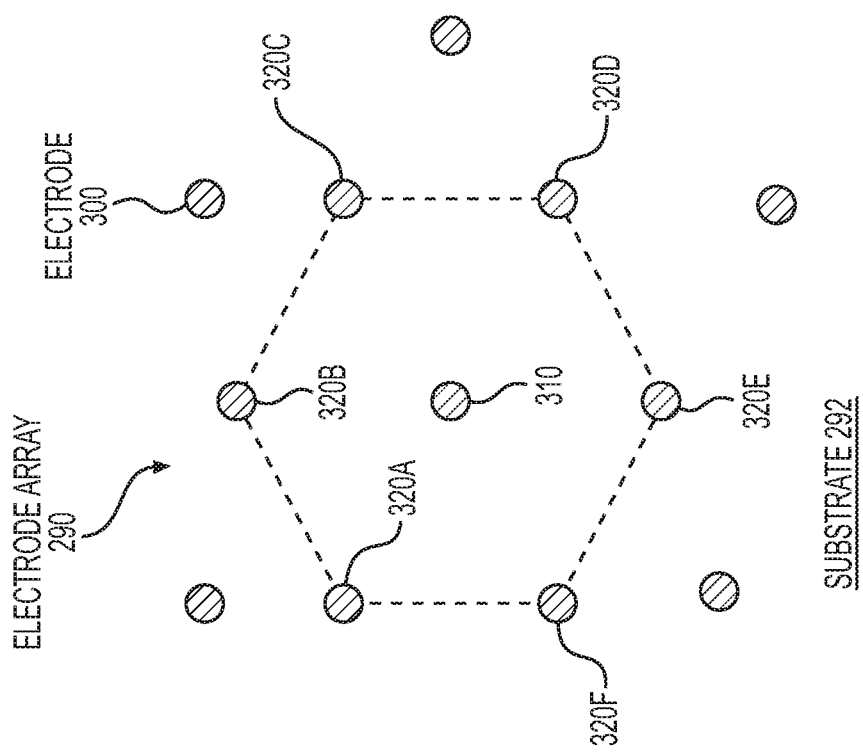
FIG. 2 is a first exemplary array of electrodes.

FIG. 2 depicts an exemplary electrode array 290, according to the present disclosure. In an aspect, an array 290 is composed of individual electrodes 300 disposed, in this example, in a regular pattern over a substrate 292. In an aspect, each electrode 300 is separately coupled (through conductive elements not shown in FIGS. 2 through 4B) to a circuit, such as described with respect to FIG. 4A, that is configured to measure an electrical parameter. In one aspect, a "virtual sensor" is created by selective connection of predetermined subsets of electrodes 300 to a common element of a circuit. In one aspect, a particular electrode 310 is connected as a center electrode, similar to electrode 110 of FIG. 1A, and six electrodes 320A-320F are connected together as a "virtual ring" electrode, similar to electrode 120 of FIG. 1A. In an aspect, two individual electrodes are individually connected to a circuit to form a virtual sensor, for example electrodes 310 and 320A are respectively connected as two electrodes of a sensor. In one aspect, one or more electrodes 300 are connected together to form one or the other electrodes of a two-electrode sensor.

Any pair of electrodes, whether composed of single electrodes or a set of electrodes coupled together to form virtual electrodes, is coupled to electronics that are configured to measures an electrical property or parameter that comprises one or more of a resistance, a capacitance, an inductance, an impedance, a reluctance, or other electrical characteristic with one or more of sensors 90, 174, 290, 430, 440, or other two-electrode sensor.

Figure 3:
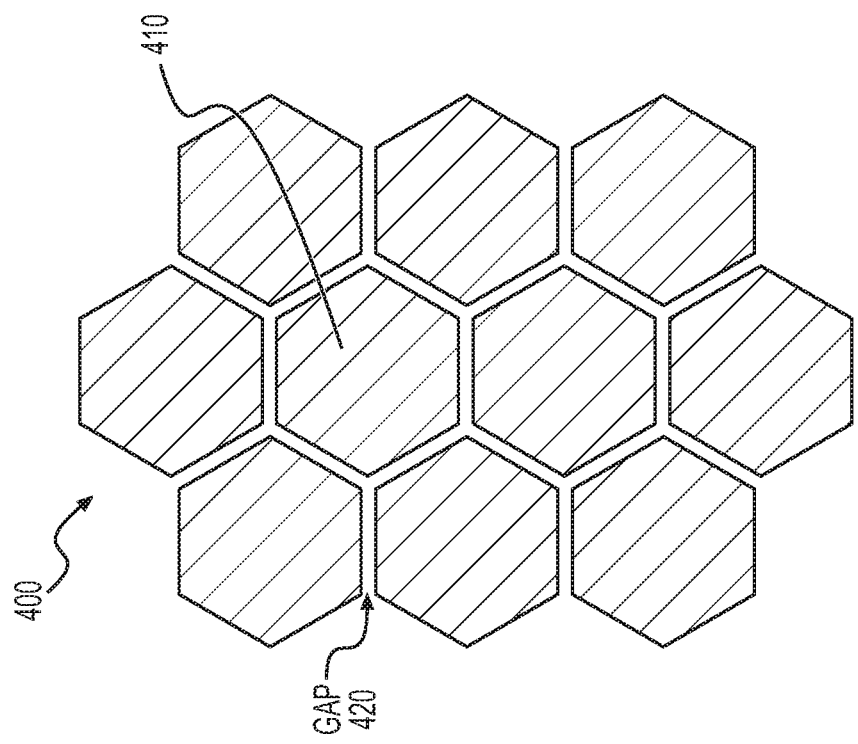
FIG. 3 is an exemplary array of electrodes according to the present disclosure.

FIG. 3 depicts another exemplary array 400 of electrodes 410, according to the present disclosure. In an aspect, each of electrodes 410 is an approximate hexagon that is separated from each of the surrounding electrodes 410 by a gap 420. In one aspect, electrodes 410 are one of circles, squares, pentagons, or other regular or irregular shapes. In an aspect, gap 420 is uniform between all electrodes 410. In one aspect, gap 420 varies between various electrodes. In an aspect, electrodes 410 may be interconnected to form virtual sensors as described below with respect to FIGS. 5A and 5B.

Figure 4B:
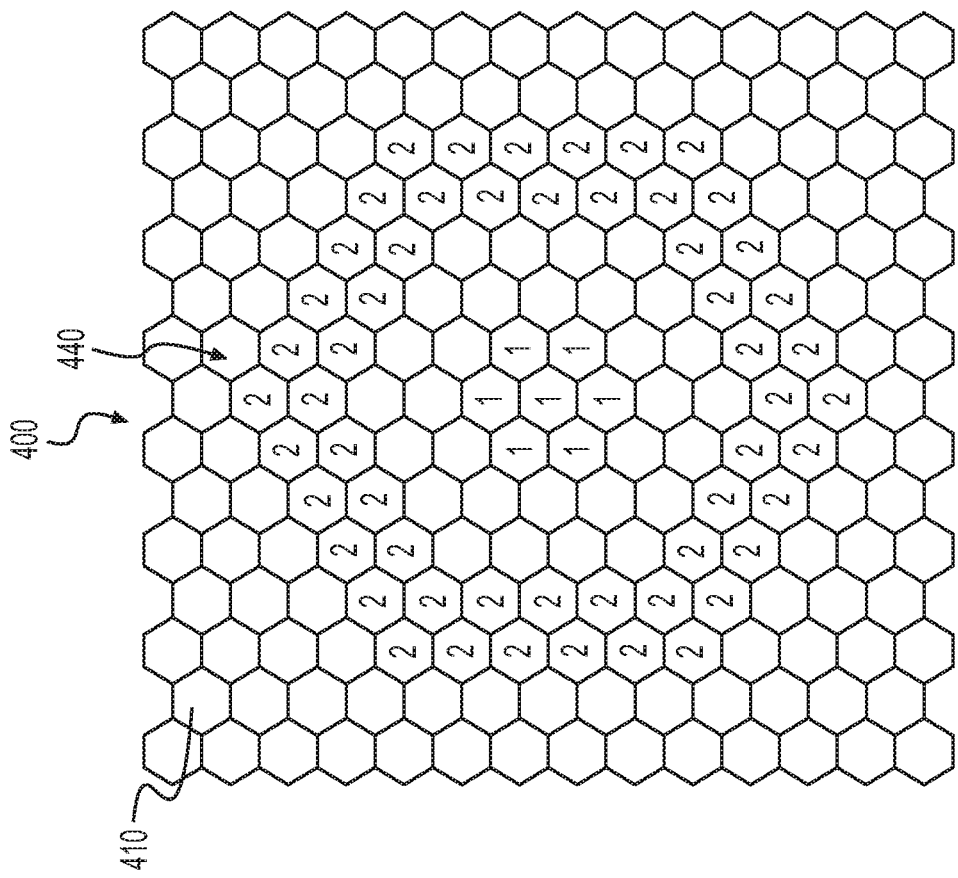
FIG. 4B illustrates a second example of how the array of electrodes disclosed in FIG. 3 is configured to form a bioimpedance sensor according to the present disclosure.
Figure 4A:
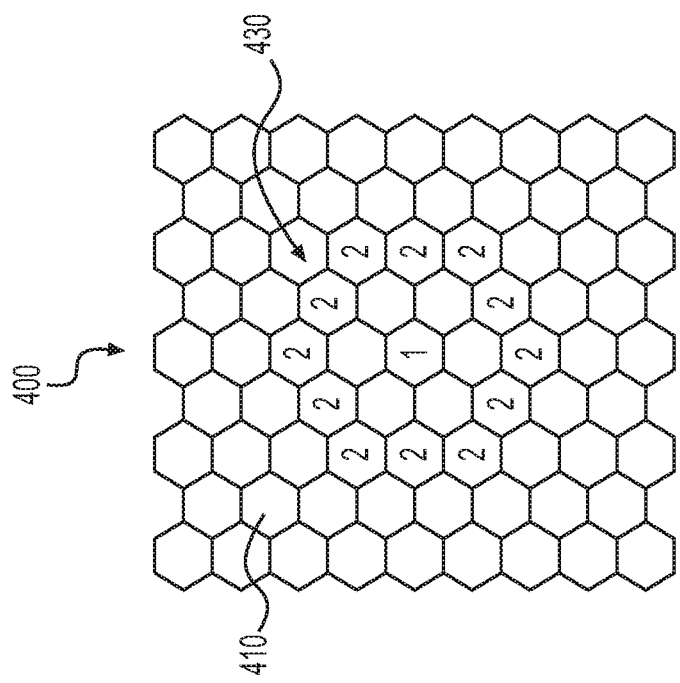
FIG. 4A illustrates a first example of how the array of electrodes disclosed in FIG. 3 is configured to form a bioimpedance sensor according to the present disclosure.

FIG. 4A depicts an array 400 of electrodes 410 that are configured, e.g. connected to a measurement circuit, to form a sensor 430, according to the present disclosure. In an aspect, a single hexagonal electrode 410 that is labeled with a "1" forms a center electrode and a ring of electrodes 410 that are marked with a "2" are interconnected to form a ring electrode. In an aspect, electrodes 410 between the center and ring electrode are electrically "floating." In one aspect, electrodes 410 between the center and ring electrode are grounded or connected to a floating ground. In one aspect, electrodes 410 that are outside the ring electrode are electrically "floating." In an aspect, electrodes 410 that are outside the virtual ring electrode are grounded or connected to a floating ground.

FIG. 4B depicts an alternate aspect where an array 400 of electrodes 410 has been configured to form a virtual sensor 440, according to the present disclosure. In an aspect, multiple electrodes 410, indicated by a "1," are interconnected to form a center electrode while a double-wide ring of electrodes, indicated by a "2," are interconnected to form a ring electrode. In one aspect, various numbers and positions of electrodes 410 are interconnected to form virtual electrodes of a variety of sizes and shapes.

Figure 5A:
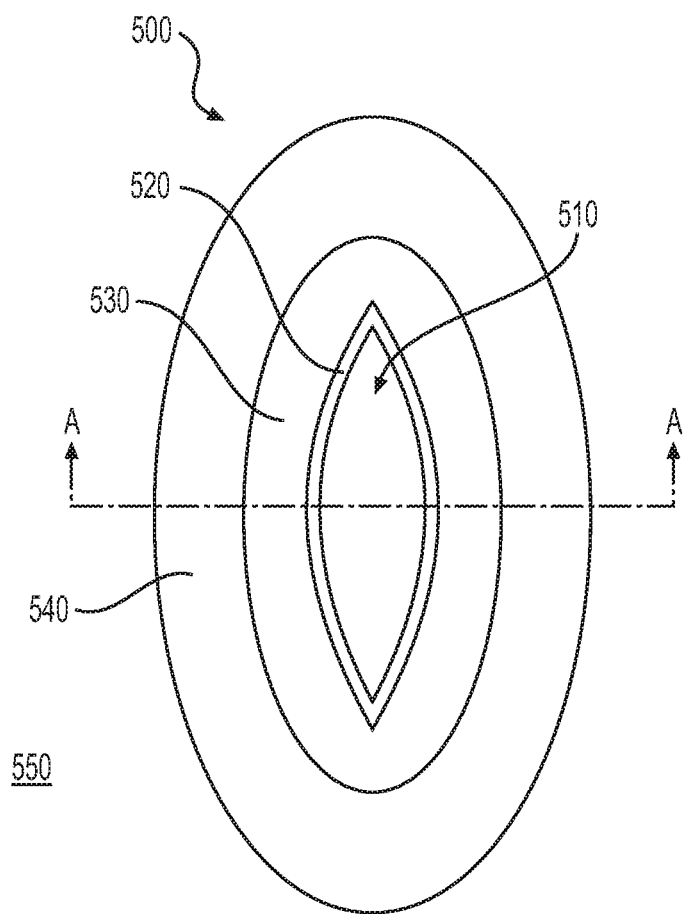
FIG. 5A depicts an example $3^{rd}$-degree burn with an open wound.

FIG. 5A depicts an example wound, in this case a $3^{rd}$-degree burn 500 with an open wound 510. Response of tissue around a $3^{rd}$-degree burn injury may comprise three zones. In an aspect, innermost zone 520 at the center of a wound will have necrosis with no perfusion of oxygen and irreversible damage due to the coagulation of proteins. In one aspect, second zone 530, also known as the "zone of stasis," is a ring around a first zone 520, where there is a decrease in perfusion and a reduction in SEM. Without being limited to a particular theory, capillaries may be nonfunctional in second zone 530, leading to increased permeability of capillaries and arterioles and subsequent ischemia reperfusion injury. There may be a chance of tissue recovery in second zone 530 if cascading release of free radicals and cellular damage leading to apoptosis can be prevented. In an aspect, surrounding a second zone 530 is a zone 540 of hyperaemia where the tissue is damaged but retains good perfusion and will generally heal. Without being limited to a particular theory, the size, shape, and depth of wound 510 as well as zones 520, 530, 540 depends on the details of the event that caused the injury. In accordance with the present disclosure, evaluation of burn depth and extent is one component on which treatment decisions are based, as inaccuracies can lead to unnecessary surgeries or patients staying for extensive lengths of time.

Figure 5B:
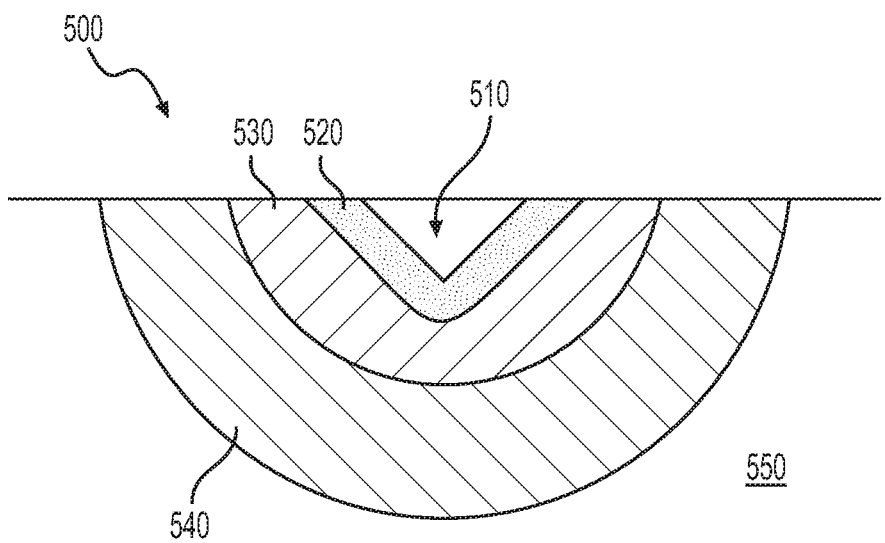
FIG. 5B depicts a cross-section of the wound of FIG. 5A.

FIG. 5B is a cross-section of a burn 500 shown in FIG. 5A, taken along line A-A in FIG. 5A. In an aspect, a first region 520 may extend below an open wound 510 as well as to the sides. In one aspect, a region 530 may extend below one or both of an open wound 510 and region 520. In an aspect, at some distance from open wound 510, there will be undamaged, or "normal," tissue 540.

In accordance with the present disclosure, burns may be characterized as "partial thickness" or "full thickness" burns, depending upon whether damaged zones 530 and 540 extend through a skin into subcutaneous tissue. Superficial partial-thickness injuries, such as a blister of a 2nd-degree burn, are viable and will generally heal with antimicrobial dressings. Deep partial-thickness wounds are more like full-thickness burns and may require surgical excision and grafting for improved functional and cosmetic outcomes. Partial-thickness wounds are complicated to treat, as it is difficult to determine if viable structures are present and capable of healing the wound. Whatever inaccuracies associated with diagnosis may affect treatment, as it is possible that a superficial burn will receive surgery for a healing wound.

Burn wounds are challenging problems as they are dynamic and have the capacity to change and progress over time. In zone 520, heating of the tissue has caused complete necrosis of the dermis and all dermal structures along with fat necrosis. Without being limited to a particular theory, moisture content of zone 520 is lower than normal and remains low after the injury due to destruction of the local blood vessels, which prevents perfusion into the necrotic region.

Without being limited to a particular theory, in zone 530, return of blood flow after the initial thermal exposure restores perfusion and oxygenation. While not being limited to theory, the restoration of oxygenation can be important for cellular survival but also initiates a cascade of events that results in production of free radicals that lead to further tissue injury. The accumulation of burn edema can occur in a two-phase pattern. In the first phase, there is a rapid increase in interstitial fluid within the first hour post-injury and approximately 80% of total edema is present at 4 hours post-injury. The second phase is marked by a gradual increase in fluid accumulation over the next 12-24 hours. In non-burn injuries, fluid movement from the capillary to the interstitium may be generally balanced by lymphatic clearance so that excess fluid does not accumulate. However, in burn injuries, while not being limited to theory, the movement of fluid and protein into the extravascular space can occur very rapidly and edema ensues because the lymphatics are unable to keep pace with the clearance of fluid and protein. Accordingly, again without being limited to a particular theory, in an aspect, the amount of edema in zone 540 is less than in zone 530, although the amount of SEM is still increased above normal. Mapping the pattern of edema allows an assessment of which tissue is at risk.

Figure 6:
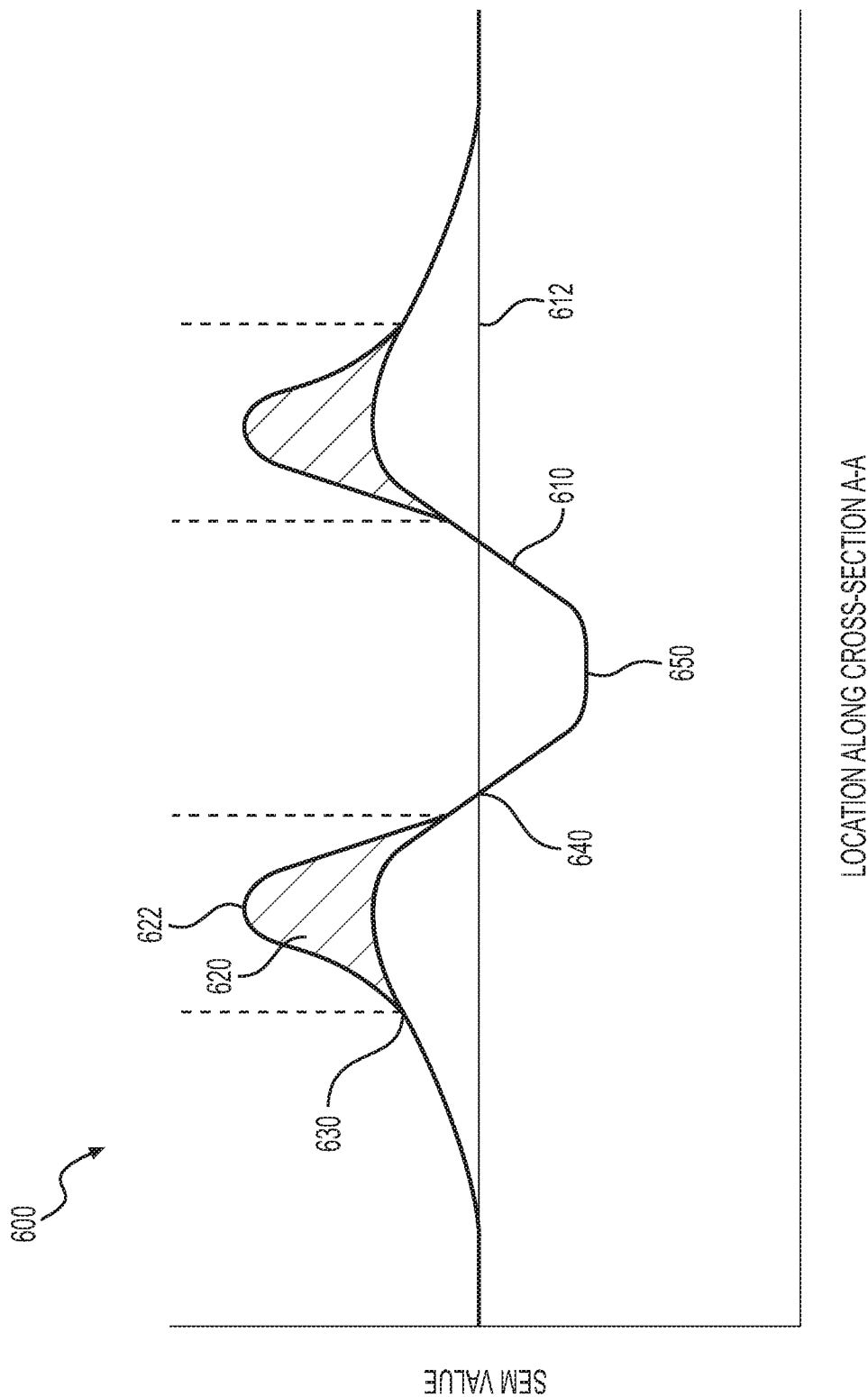
FIG. 6 provides an example plot 600 of how SEM values may vary across the wound of FIG. 5A, according to the present disclosure.

FIG. 6 depicts an example plot 600 of how SEM values may vary across burn 500, according to the present disclosure. SEM values taken along cross-section A-A have been plotted as curve 610, with the x-axis being the location along cross-section A-A and the y-axis being the SEM value. A reference line 612 indicates normal tissue SEM value, which may a standard reference value or a measurement of known undamaged tissue on the patient.

In an aspect, curve 610 generally shows a region 620 where a SEM value is greater than reference line 612. In one aspect, curve 610 in region 620 may be only slightly raised, as indicated by the bottom of the shaded region, or may be significantly increased as indicated by the top of the shaded region 620. In an aspect, a peak value 622 of region 620 is an indication of the degree or depth of the damage in zone 530.

In one aspect, point 630 on curve 610 indicates a transition from zone 530 to zone 540. In an aspect, a SEM value is higher than reference line 612 but not so elevated as to indicate a risk that a tissue will not recover. In one aspect, location of a transition from zone 530 to zone 540 may be identified on curve 610 as the x-axis position of a point 630 using a known magnitude of a SEM value. In an aspect, the magnitude of a SEM value at point 630 may be a value selected from the group consisting of a predetermined value, a predetermined increase above a reference SEM value, a percentage of a reference SEM value, a percentage of peak value 622, and other value determined from curve 610.

In an aspect, a predetermined SEM value may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined SEM value may range from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined SEM value may range from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined SEM value may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In an aspect, a predetermined SEM value can be scaled by a factor or a multiple based on the values provided herein.

In an aspect, a predetermined increase may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined increase may range from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined increase may range from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined increase may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In an aspect, a predetermined increase can be scaled by a factor or a multiple based on the values provided herein.

In one aspect, a reference SEM value is represented by a reference line 612. In an aspect, a reference SEM value may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a reference SEM value may range from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a reference SEM value may range from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a reference SEM value may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In an aspect, a reference SEM value can be scaled by a factor or a multiple based on the values provided herein.

In an aspect, a peak value may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a peak value may range from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a peak value may range from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a peak value may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In an aspect, a peak value can be scaled by a factor or a multiple based on the values provided herein.

One or more regions may be defined on a body. In an aspect, measurements made within a region are considered comparable to each other. A region may be defined as an area on the skin of the body where measurements may be taken at any point within the area. In an aspect, a region corresponds to an anatomical region (e.g., heel, ankle, lower back). In an aspect, a region may be defined as a set of two or more specific points relative to anatomical features where measurements are taken only at the specific points. In an aspect, a region may comprise a plurality of non-contiguous areas on the body. In an aspect, the set of specific locations may include points in multiple non-contiguous areas.

In an aspect, a region is defined by surface area. In an aspect, a region may be, for example, between 5 and 200 $cm^2$, between 5 and 100 $cm^2$, between 5 and 50 $cm^2$, or between 10 and 50 $cm^2$, between 10 and 25 $cm^2$, or between 5 and 25 $cm^2$.

In an aspect, measurements may be made in a specific pattern or portion thereof. In an aspect, the pattern of readings is made in a pattern with the target area of concern in the center. In an aspect, measurements are made in one or more circular patterns of increasing or decreasing size, T-shaped patterns, a set of specific locations, or randomly across a tissue or region. In an aspect, a pattern may be located on the body by defining a first measurement location of the pattern with respect to an anatomical feature with the remaining measurement locations of the pattern defined as offsets from the first measurement position.

In an aspect, a plurality of measurements are taken across a tissue or region and the difference between the lowest measurement value and the highest measurement value of the plurality of measurements is recorded as a delta value of that plurality of measurements. In an aspect, 3 or more, 4 or more, 5 or more, 6 or more, 7 or more, 8 or more, 9 or more, or 10 or more measurements are taken across a tissue or region.

In an aspect, a threshold may be established for at least one region. In an aspect, a threshold of 0.2, 0.3, 0.4, 0.5, 0.6, 0.7, 0.8, 0.9, or other value may be established for the at least one region. In an aspect, a delta value is identified as significant when the delta value of a plurality of measurements taken within a region meets or exceeds a threshold associated with that region. In an aspect, each of a plurality of regions has a different threshold. In an aspect, two or more regions may have a common threshold.

In an aspect, a threshold has both a delta value component and a chronological component, where a delta value is identified as significant when the delta value is greater than a predetermined numerical value for a predetermined portion of a time interval. In an aspect, the predetermined portion of a time interval is defined as a minimum of X days where a plurality of measurements taken that day produces a delta value greater than or equal to the predetermined numerical value within a total of Y contiguous days of measurement. In an aspect, the predetermined portion of a time interval may be defined as 1, 2, 3, 4, or 5 consecutive days on which a plurality of measurements taken that day produces a delta value that is greater than or equal to the predetermined numerical value. In an aspect, the predetermined portion of a time interval may be defined as some portion of a different specific time period (weeks, month, hours etc.).

In an aspect, a threshold has a trending aspect where changes in the delta values of consecutive pluralities of measurements are compared to each other. In an aspect, a trending threshold is defined as a predetermined change in delta value over a predetermined length of time, where a determination that the threshold has been met or exceeded is significant. In an aspect, a determination of significance will cause an alert to be issued. In an aspect, a trend line may be computed from a portion of the individual measurements of the consecutive pluralities of measurements. In an aspect, a trend line may be computed from a portion of the delta values of the consecutive pluralities of measurements.

In an aspect, the number of measurements taken within a single region may be less than the number of measurement locations defined in a pattern. In an aspect, a delta value will be calculated after a predetermined initial number of readings, which is less than the number of measurement locations defined in a pattern, have been taken in a region and after each additional reading in the same region, where additional readings are not taken once the delta value meets or exceeds the threshold associated with that region.

In an aspect, the number of measurements taken within a single region may exceed the number of measurement locations defined in a pattern. In an aspect, a delta value will be calculated after each additional reading.

In an aspect, a quality metric may be generated for each plurality of measurements. In an aspect, this quality metric is chosen to assess the repeatability of the measurements. In an aspect, this quality metric is chosen to assess the skill of the clinician that took the measurements. In an aspect, the quality metric may include one or more statistical parameters, for example an average, a mean, or a standard deviation. In an aspect, the quality metric may include one or more of a comparison of individual measurements to a predefined range. In an aspect, the quality metric may include comparison of the individual measurements to a pattern of values, for example comparison of the measurement values at predefined locations to ranges associated with each predefined location. In an aspect, the quality metric may include determination of which measurements are made over healthy tissue and one or more evaluations of consistency within this subset of "healthy" measurements, for example a range, a standard deviation, or other parameter.

In one aspect, a measurement, for example, a threshold value, is determined by SEM Scanner Model 200 (Bruin Biometrics, LLC, Los Angeles, Calif.). In another aspect, a measurement is determined by another SEM scanner.

In an aspect, a measurement value is based on a capacitance measurement by reference to a reference device. In an aspect, a capacitance measurement can depend on the location and other aspects of any electrode in a device. Such variations can be compared to a reference SEM device such as an SEM Scanner Model 200 (Bruin Biometrics, LLC, Los Angeles, Calif.). A person of ordinary skill in the art understands that the measurements set forth herein can be adjusted to accommodate a difference capacitance range by reference to a reference device.

In an aspect, a percentage in accordance with the present disclosure may range from 0-100%, such as 0-50%, 25-75%, 50-100%, 0-10%, 5-15%, 10-20%, 15-25%, 20-30%, 25-35%, 30-40%, 35%-45%, 40-50%, 0-25%, 15-35%, 25-50%, 45-55%, 50-60%, 55-65%, 60-70%, 65-75%, 40-55%, 50-75%, 70-80%, 75%-85%, 80-90%, 85-95%, 90-100%, 65-85%, or 75-100%. In one aspect, a percentage in accordance with the present disclosure may be about 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%.

In an aspect, point 640 on curve 610 indicates a transition from zone 530, where edema has occurred, to zone 520, where the tissue has a moisture content below normal. In one aspect, a measured SEM value that equals the normal value of reference line 612 indicates that a portion of a sensor is over tissue having a higher-than-normal moisture content while the remaining portion of the sensor is over tissue having a lower-than-normal moisture content. In an aspect, point 640 on line A-A is approximately the location of the edge of zone 520. If it is desirable to excise the necrotic tissue from a patient, marking the skin at this point provides a reference to the surgeon of the edge of necrotic tissue.

In one aspect, successive measurements of SEM values at one or more points proximate to an open wound 510, for example at 30 minute intervals for the first 4 hours, can provide information regarding the degree of damage to the tissue. In an aspect, successive measurements can be performed at approximately 5 minute intervals, 10 minute intervals, 15 minute intervals, 20 minute intervals, 25 minute intervals, 35 minute intervals, 40 minute intervals, 45 minute intervals, 50 minute intervals, 60 minute intervals, 90 minute intervals, or 120 minute intervals. In one aspect, successive measurement can be performed at time intervals for the first 1 hour, 2 hours, 3 hours, 5 hours, 6 hours, 7 hours, 8 hours, 9 hours, 10 hours, 11 hours, or 12 hours after an injury. In an aspect, the value and position of point 622 over the first 4 hours post-injury may indicate the depth of the burn and the risk of tissue depth in certain areas. Outward progression of the peak SEM values on the x-axis may indicate the severity of the reperfusion damage.

In one aspect, measurements of SEM values may be taken with a single-sensor device, such as a SEM scanner 170 of FIG. 1B, and logged, plotted, and assessed.

Other types of wounds, for example a cut, may suffer from zones of tissue death proximate to open wound 510. As the level of edema is still an indication of tissue viability, the same sensing and categorization method will provide valuable information to a clinician treating the injury. Thus, the methods and apparatus described for the example burn may also be applicable to other types of injury.

The methods and apparatus disclosed herein may also be used to track the healing process of injuries such as burns, cuts, ulcers, and other types of tissue damage. Closure of the skin over a wound is not the end of the healing process, and it may take a year after the skin closes for the sub-epidermal tissue to return to its original state. Periodic assessment of the site of the original wound will show whether the healing is continuing to progress or has halted or reversed. As an example, pressure ulcers are known to suffer a high incidence of recurrence at the same location as a first ulcer. This is thought to be a result of continued pressure at the site combined with a weakened tissue structure as a result of incomplete healing. In the absence of continued measurement of the tissue state, for example with a SEM scanner, it is likely that a caregiver would consider a closed wound as a healed wound and not continue the therapy that would prevent the recurrence. Measurements of surrounding tissue at sites away from the original wound can serve as a reference of what "normal" tissue measurements. The trend of changes, or lack thereof, of measurements at the former wound site against this reference provides a continued assurance that the tissue is moving toward a fully healed condition.

This monitoring of tissue improvement after the wound has healed is also useful to monitor the performance and efficacy of wound-healing therapies. As an example, an electro-stimulus device may be used once a wound has closed in order to accelerate the healing process of the underlying tissue. The progress of the healing is likely to be difficult if not impossible to assess manually or visually. A SEM scanning device could be used to establish one or more of a SEM measurement at the site of the closed wound, periodic measurements and trend analysis to verify the effectiveness of the healing device, and measurement of adjacent tissue as a reference of fully healed tissue. In certain embodiments, adjustments may be made to the healing device, for example a change in the frequency or voltage of an electro-stimulus device, based on the measurements or the trend of the measurements made by an SEM scanner. In certain embodiments, the use of a healing device or therapy may be halted or replaced with a different device or therapy based on the SEM measurements or trend. In certain embodiments, the wound may be judged to be "healed" based on the SEM measurement and healing therapies may be halted, modified, or replaced with preventative therapies. In certain embodiments, the difference between a current SEM reading at the site of the wound and a reference value from nearby healthy tissue is a metric of the degree of recovery of the tissue at the wound site, where a zero difference is fully healed and restored to original condition.

Figure 7:
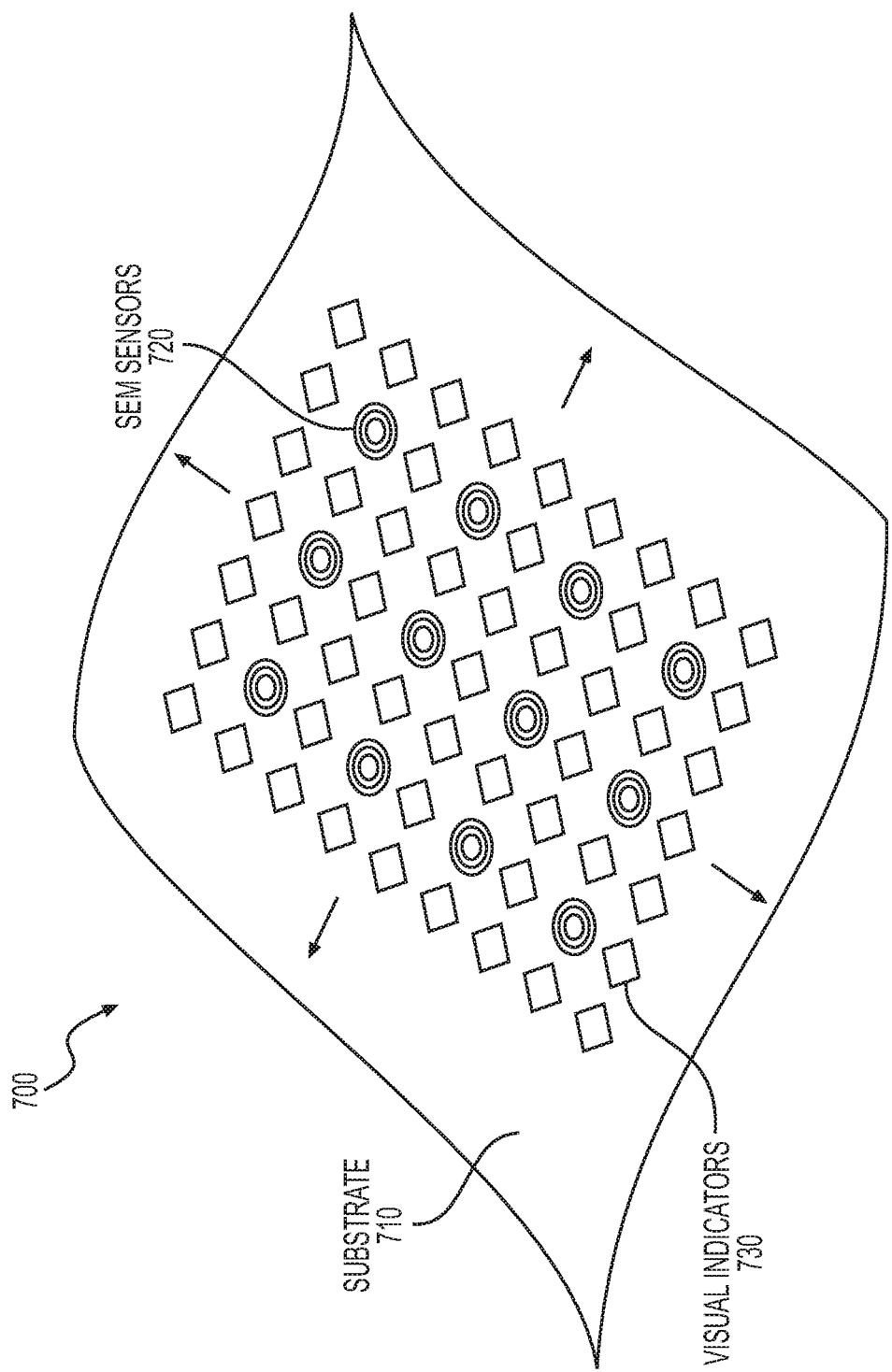
FIG. 7 discloses a first exemplary aspect of an SEM sensing apparatus according to the present disclosure.

FIG. 7 depicts an aspect of a SEM sensing apparatus 700, according to the present disclosure. In one aspect, a flexible substrate 710 has a plurality of SEM sensors 720 arranged on a common surface of substrate 710. In an aspect, sensors 720 comprise toroidal sensors 90 as shown in FIG. 1A. In one aspect, sensors 720 comprise an electrode array 290 as shown in FIG. 2. In an aspect, sensors 720 comprise an electrode array 400 as shown in FIG. 3. In one aspect, sensors 720 are coupled to electronics (not shown in FIG. 7) that provide excitation and measure an SEM value of the tissue below the respective sensors 720.

In an aspect, SEM sensing apparatus 700 comprises visual indicators 730 that are arranged on a substrate 710. In one aspect, visual indicators 730 are on a first surface of a substrate 710 while sensors 720 are on a second surface of substrate 710 that is opposite the first surface. In an aspect, visual indicators 730 are disposed between at least some pairs of sensors 720. In one aspect, visual indicators 730 may be light emitting devices (LEDs). In an aspect, visual indicators 730 may emit a single color of light. In an aspect, visual indicators 730 may selectably emit one of a plurality of colors of light. In one aspect, visual indicators 730 are selectable to be on or off. In an aspect, visual indicators 730 are coupled to electronics (not shown in FIG. 7) that provide excitation and selectable control of visual indicators 730.

In an aspect, electronics of the present disclosure actuate each visual indicator 730 with a color of light selected based on the SEM values measured by sensors 90 disposed on each side of the respective visual indicator 730. This provides a color-coded map of the various zones 520, 530, and 540 for a given wound 500.

In one aspect, visual indicators 730 may be disposed on the same surface of substrate 710 as sensors 720. In an aspect, visual indicators 730 comprise marking element (not visible in FIG. 7) that can selectably mark the skin of a patient on which a SEM sensing apparatus 700 is placed. In an aspect, electronics of the present disclosure can actuate the marking element of visual indicators 720 that are disposed along one or more of the boundaries between zones of FIGS. 5A and 5B. In one aspect, electronics of the present disclosure may actuate the marking elements to mark the boundary between zone 520 and zone 530, indicating the outer edge of non-viable tissue.

Figure 8A:
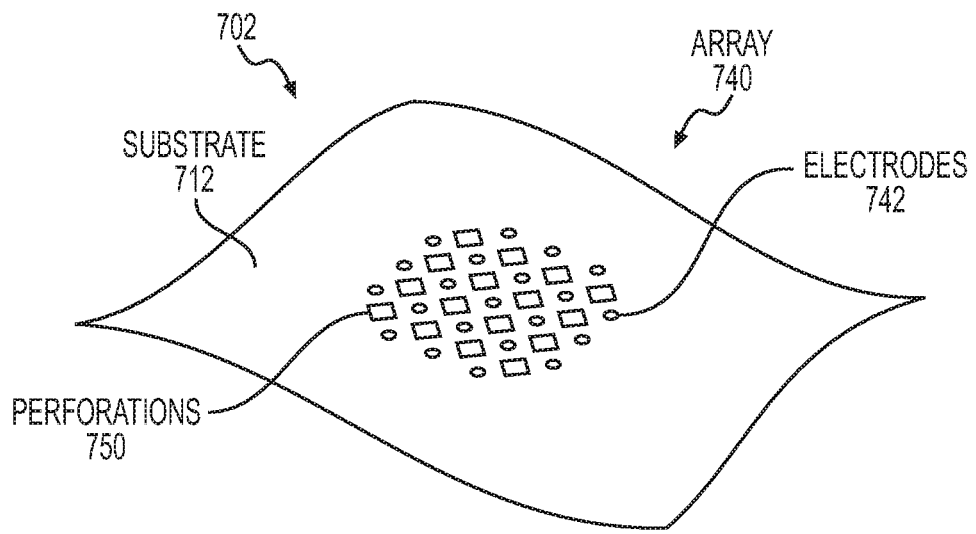
FIG. 8A discloses a second exemplary aspect of an SEM sensing apparatus according to the present disclosure.
Figure 8B:
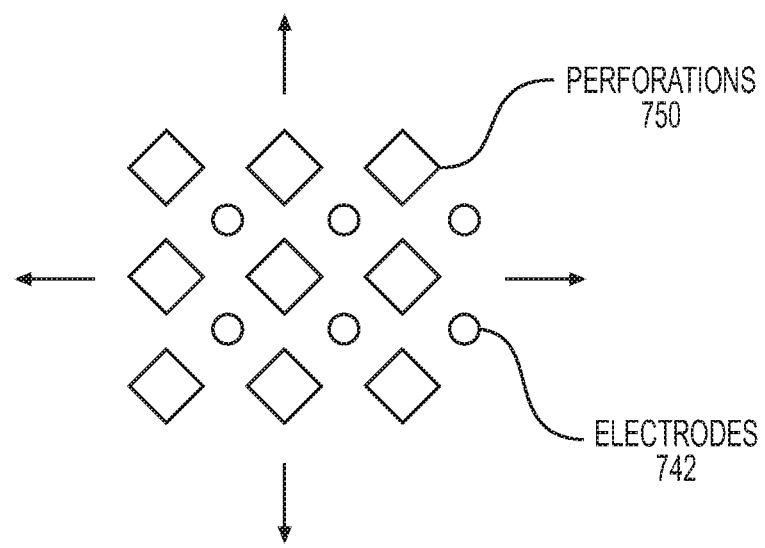
FIG. 8B discloses a third exemplary aspect of an SEM sensing apparatus according to the present disclosure.

FIGS. 8A and 8B disclose an aspect of a SEM sensing assembly 702, according to the present disclosure. In one aspect, an array 740 of electrodes 742 is disposed on a substrate 712. In an aspect, electrodes 742 are similar to electrodes 300 of FIG. 2. In one aspect, electrodes 742 are similar to electrodes 410 of FIG. 3.

In an aspect, a SEM sensing apparatus 702 comprises a plurality of perforations 750. In one aspect, perforations 750 are disposed between pairs of electrodes 742, as shown in FIG. 8B. In use, SEM sensing apparatus 702 can be placed on the skin of a patient over a wound and a clinician marks the skin of the patient as guided by the SEM values measured between various pairs of electrodes 742.

In an aspect, a SEM sensing apparatus 700 may comprise both visual indicators 730 and perforations 750, allowing a clinician to mark the skin of a patient as guided by the colors of various visual indicators 730.

Figure 9:
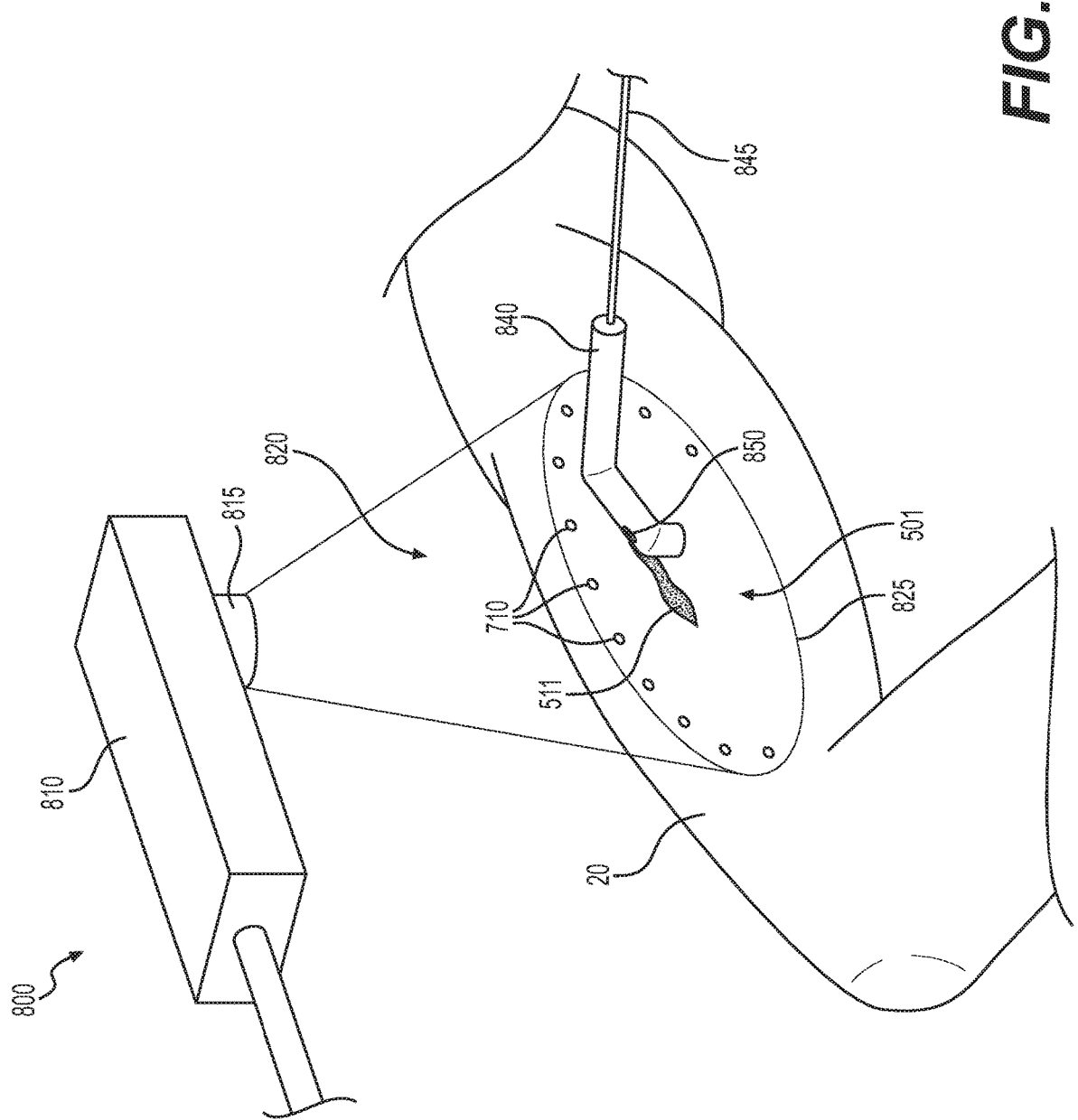
FIG. 9 discloses an aspect of an apparatus for mapping areas of damage according to the present disclosure.

FIG. 9 discloses an aspect of an apparatus 800 for mapping areas of damage around a wound, according to the present disclosure. In one aspect, a patient's arm 20 has a burn 501 with an open wound 511. In an aspect, apparatus 800 comprises an instrument head 810 overhanging arm 20 with an optical system 815 that comprises a camera (not visible in FIG. 9) that observes area 825 on arm 20 and a projector (not visible in FIG. 9) that can project one or more images onto area 825, which encompasses wound 511 as well as tissue around wound 511. In one aspect, a SEM sensing apparatus 840 is coupled to electronics (not shown in FIG. 9) that also control optical system 815. In an aspect, SEM sensing apparatus 840 is coupled to electronics of the present disclosure through a cable 845. In an aspect, SEM sensing apparatus 840 comprises a wireless linkage in place of cable 845. In one aspect, SEM sensing apparatus 840 comprises a fiducial 850 that is visible to a camera while apparatus 800 is in use. In an aspect, SEM sensing apparatus 840 comprises a single bioimpedance sensor and, therefore, measures the ECF at a single point at a time.

In use, a user can make multiple measurements with a SEM sensing apparatus 840 in area 825. At the time of each measurement, a camera can observe and record the position of fiducial 850 in its field of view. In an aspect, reference marks (not shown in FIG. 9) may be made on arm 20 to record the position of arm 20 in the field of view and enable movement of arm 20 during an assessment. As the set of measurements increases, electronics of the present disclosure determines the location of a boundary between tissue types, for example a boundary between viable and non-viable tissue, and causes the projector to project indicating images along this boundary. In FIG. 9, these images are shown as dots 710. In an aspect, a projected image may comprise lines, areas of color, areas shading from a first color to a second color, areas shading from one intensity of a color to a different intensity of the same color, or other visual indication that provides guidance as to the condition of the tissue in area 825.

In one aspect, electronics of the present disclosure may be coupled to a printer (not shown in FIG. 9) and can cause the printer to produce a picture of arm 20 with wound 511 taken by a camera and overlaid with markings equivalent to those described as provided by a projector. In an aspect, measurements may be repeated with SEM sensing apparatus 800 and new pictures printed, thereby creating a pictorial history of the progression of damage around a wound. In one aspect, electronics of the present disclosure may be coupled to a storage device, for example a server, and configured to store information regarding an image of arm 20 and wound 511 as well as measurements and locations of the measurements made by a SEM sensing apparatus 840 at one or more times.

From the foregoing, it will be appreciated that the present invention can be embodied in various ways, which include but are not limited to the following:

Embodiment 1

An apparatus for mapping areas of damage around a wound, the apparatus comprising: a plurality of electrodes embedded on a substrate configured to be placed over an area of tissue that includes the wound, where combinations of the electrodes are capable of forming a plurality of virtual capacitive sensors and each of the virtual capacitive sensors is configured to measure a capacitance of a region of tissue proximate to the respective virtual capacitive sensor, a plurality of visual indicators embedded on the substrate, a drive circuit electronically coupled to the electrodes and visual indicators, a processor electronically coupled to the drive circuit, and a non-transitory computer-readable medium electronically coupled to the processor and comprising instructions stored thereon that, when executed on the processor, perform the steps of: receiving information regarding the measured capacitance from a subset of the plurality of virtual capacitive sensors via the drive circuit, determining a boundary between viable and non-viable tissue, and activating via the drive circuit a portion of the plurality of visual indicators to indicate the boundary.

Embodiment 2

The apparatus of embodiment 1, where the substrate comprises a plurality of perforations that allow marking of the tissue along the boundary.

Embodiment 3

The apparatus of embodiment 1, where the circuit is configured to selectively drive pairs of the electrodes and measure the capacitance between each of the pairs of electrodes.

Embodiment 4

The apparatus of embodiment 3, where each of the selectively driven pairs of electrodes form one of the plurality of virtual capacitive sensors.

Embodiment 5

The apparatus of embodiment 1, where the circuit is configured to selectively drive subsets of the plurality of electrodes to form a virtual center electrode and a virtual ring electrode and measuring the capacitance between the virtual center electrode and the virtual ring electrode.

Embodiment 6

The apparatus of embodiment 5, where each of the plurality of virtual capacitive sensors comprises a virtual center electrode and a virtual ring electrode.

Embodiment 7

The apparatus of embodiment 1, where the instructions further comprise the steps of: converting each measured capacitance to an associated sub-epidermal moisture (SEM) value that is associated with the virtual capacitive sensor used to measure the capacitance, comparing a first portion of the SEM values to a first threshold, and identifying regions of tissue corresponding to the virtual capacitive sensors that are associated with SEM values that are greater than the first threshold as viable.

Embodiment 8

The apparatus of embodiment 7, where the instructions further comprise the steps of: comparing a second portion of the SEM values to a second threshold, and identifying regions of tissue corresponding to the virtual capacitive sensors that are associated with SEM values that are less than the second threshold as non-viable.

Embodiment 9

The apparatus of embodiment 7, where each of the plurality of visual indicators independently comprises a first mode of display and a second mode of display.

Embodiment 10

The apparatus of embodiment 9, where the instructions further comprise the steps of: activating a third portion of the plurality of visual indicators in the first mode of display to indicate the regions of tissue that are viable, and activating a fourth portion of the plurality of visual indicators in the second mode of display to indicate the regions of tissue that are non-viable.

Embodiment 11

The apparatus of embodiment 9, where: the visual indicators are light-emitting devices (LEDs), the first mode of display comprises emitting light having a first characteristic, and the second mode of display comprises emitting light having a second characteristic.

Embodiment 12

The apparatus of embodiment 11, where: the first characteristic comprises a first spectral content, and the second characteristic comprises a second spectral content that is different from the first spectral content.

Embodiment 13

An apparatus for determining a depth of a burn wound, the apparatus comprising: a pair of electrodes capable of forming a capacitive sensor that is configured to measure a capacitance of a region of tissue proximate to the pair of electrodes, a drive circuit electronically coupled to the capacitive sensor, a processor electronically coupled to the drive circuit, and a non-transitory computer-readable medium electronically coupled to the processor and comprising instructions stored thereon that, when executed on the processor, perform the steps of: receiving information regarding the measured capacitance from the capacitive sensor via the drive circuit, comparing the information to a data array comprising pairs of capacitances and depths of burns, and determining the depth of the burn wound associated with the measured capacitance.

Embodiment 14

The apparatus of embodiment 13, where: the step of receiving information regarding the measured capacitance comprises: receiving a first capacitance measured at a first location of known unaffected tissue, receiving a second capacitance measured at a second location within the burn wound, and determining a capacitance difference between the first and second capacitances; the data array comprises pairs of capacitance differences and depths of burns; the step of comparing the information to the data array comprises comparing the capacitive difference to the data array; and the step of determining the depth of the burn wound comprises identifying the depth of the burn wound associated with the capacitive difference.

Embodiment 15

The apparatus of embodiment 13, where: the instructions further comprise the step of converting each measured capacitance to an associated sub-epidermal moisture (SEM) value, the data array comprises pairs of SEM values and depths of burns, the step of comparing the information to the data array comprises comparing the SEM value to the data array, and the step of determining the depth of the burn wound comprises identifying the depth of the burn wound associated with the SEM value.

Embodiment 16

An apparatus for mapping areas of damage around a wound, the apparatus comprising: a plurality of electrodes embedded on a substrate configured to be placed over a portion of an area of tissue that includes the wound, where pairs of the electrodes are capable of forming a capacitive sensor that is configured to measure a capacitance of a region of tissue proximate to the capacitive sensor, a projector capable of projecting a visual indicator onto the area of tissue that includes the wound, a drive circuit electronically coupled to the plurality of electrodes and the projector, a processor electronically coupled to the drive circuit, and a non-transitory computer-readable medium electronically coupled to the processor and comprising instructions stored thereon that, when executed on the processor, perform the steps of: receiving information regarding the measured capacitance from one or more of the formed capacitive sensors, determining a first boundary between a first type of tissue and a second type of tissue, and causing the projector to project the visual indicator to indicate the boundary.

Embodiment 17

The apparatus of embodiment 16, where the first type of tissue is a viable tissue, and the second type of tissue is a non-viable tissue.

Embodiment 18

The apparatus of embodiment 17, where the first boundary is identified by: converting each measured capacitance to an associated sub-epidermal moisture (SEM) value that is associated with the capacitive sensor used to measure the capacitance, identifying regions of tissue corresponding to the capacitive sensors that are associated with SEM values that are greater than a threshold as viable, identifying regions of tissue corresponding to the capacitive sensors that are associated with SEM values that are lesser than the threshold as non-viable; and marking a first boundary between the viable and non-viable regions.

Embodiment 19

The apparatus of embodiment 16, where the instructions further comprise the step of determining a second boundary between the second type of tissue and a third type of tissue.

Embodiment 20

The apparatus of embodiment 19, where the first type of tissue is a necrotic tissue, where the second type of tissue is a tissue in a zone of stasis, and where the third type of tissue is a tissue in a zone of hyperaemia.

Embodiment 21

The apparatus of embodiment 20, where the first and second boundaries are identified by: converting each measured capacitance to an associated sub-epidermal moisture (SEM) value that is associated with the capacitive sensor used to measure the capacitance, identifying regions of tissue corresponding to the capacitive sensors that are associated with SEM values that are lesser than a first threshold as a necrotic tissue, marking the first boundary on an outer edge of the necrotic tissue regions, identifying regions of tissue in a zone of stasis comprising tissue immediately surrounding the regions of necrotic tissue and corresponding to the capacitive sensors that are associated with SEM values that are greater than the first threshold up to and including locations associated with a peak SEM value, and tissue immediately surrounding the locations associated with the peak SEM value and corresponding to the capacitive sensors that are associated with SEM values that are greater than a second threshold, marking the second boundary on an outer edge of the zone of stasis; and identifying regions of tissue in a zone of hyperaemia comprising tissue immediately surrounding the zone of stasis and corresponding to the capacitive sensors that are associated with SEM values that are lesser than the second threshold but greater than the first threshold.

Embodiment 22

A method for mapping areas of damage around a wound, the method comprising: obtaining capacitance measurements over an area of a tissue including the wound using a plurality of electrodes; converting each measured capacitance to an associated sub-epidermal moisture (SEM) value; and marking a first boundary encompassing regions of tissue associated with SEM values that are lesser than a first threshold.

Embodiment 23

The method of embodiment 22, further comprising: marking a second boundary surrounding the first boundary and encompassing regions of tissues associated with SEM values that are greater than the first threshold up to and including locations associated with a peak SEM value, and tissue immediately surrounding the locations associated with the peak SEM value and are associated with SEM values that are greater than a second threshold.

While the invention has been described with reference to particular aspects, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular aspects disclosed but that the invention will include all aspects falling within the scope and spirit of the appended claims.

We claim:

1. An apparatus for mapping regions of damage around a wound, said apparatus comprising:
    a plurality of electrodes embedded on a substrate configured to be placed over an area of tissue that includes the wound, wherein combinations of said plurality of electrodes are capable of forming a plurality of virtual capacitive sensors, each of said virtual capacitive sensors comprising more than two electrodes of said plurality of electrodes and configured to measure a capacitance of a region of tissue proximate to said respective virtual capacitive sensor, a plurality of visual indicators embedded on said substrate, wherein each visual indicator of said plurality of visual indicators is disposed between at least two electrodes, wherein each of said plurality of visual indicators is a light-emitting diode (LED) comprising a plurality of modes of display based on said capacitance measured by said virtual capacitive sensors disposed on each side of said respective visual indicator, a drive circuit electronically coupled to said plurality of electrodes and plurality of visual indicators, a processor electronically coupled to said drive circuit, and a non-transitory computer-readable medium electronically coupled to said processor and comprising instructions stored thereon that, when executed on said processor, perform the steps of:

receiving information regarding said measured capacitance from a subset of said plurality of virtual capacitive sensors via said drive circuit, determining a boundary between viable and non-viable tissue, and activating via said drive circuit a portion of said plurality of visual indicators to indicate said boundary.

2. The apparatus of claim 1, wherein said substrate comprises a plurality of perforations that allow marking of said region of tissue along said boundary.

3. The apparatus of claim 1, wherein said drive circuit is configured to selectively drive pairs of said electrodes and measure said capacitance between each of said pairs of electrodes.

4. The apparatus of claim 3, wherein each of said selectively driven pairs of electrodes form one of said plurality of virtual capacitive sensors.

5. The apparatus of claim 1, wherein said drive circuit is configured to selectively drive subsets of said plurality of electrodes to form a virtual center electrode and a virtual ring electrode and measuring said capacitance between said virtual center electrode and said virtual ring electrode.

6. The apparatus of claim 5, wherein each of said plurality of virtual capacitive sensors comprises a virtual center electrode and a virtual ring electrode.

7. The apparatus of claim 1, wherein said instructions further comprise the steps of:

converting each of said measured capacitance to an associated sub-epidermal moisture (SEM) value that is associated with said virtual capacitive sensor used to measure said capacitance, comparing a first subset of said SEM values to a first threshold, and identifying regions of viable tissue corresponding to said virtual capacitive sensors that are associated with SEM values that are greater than said first threshold.

8. The apparatus of claim 7, wherein said instructions further comprise the steps of:

comparing a second subset of said SEM values to a second threshold, and identifying regions of non-viable tissue corresponding to said virtual capacitive sensors that are associated with SEM values that are less than said second threshold.

9. The apparatus of claim 7, wherein said plurality of modes of display comprises a first mode of display and a second mode of display.

10. The apparatus of claim 9, wherein said instructions further comprise the steps of:

activating a first portion of said plurality of visual indicators in said first mode of display to indicate said regions of viable tissue, and activating a second portion of said plurality of visual indicators in said second mode of display to indicate said regions of non-viable tissue.

11. The apparatus of claim 9, wherein:

said first mode of display comprises emitting light having a first characteristic, and said second mode of display comprises emitting light having a second characteristic.

12. The apparatus of claim 11, wherein:

said first characteristic comprises a first spectral content, and said second characteristic comprises a second spectral content that is different from said first spectral content.

* * * * *